(12) United States Patent
Zeiger et al.

(10) Patent No.: US 10,774,389 B2
(45) Date of Patent: *Sep. 15, 2020

(54) ALTERNATIVE SPLICE VARIANT PATTERNS OF HUMAN TELOMERASE REVERSE TRANSCRIPTASE (HTERT) IN THYROID TUMORS TO DISTINGUISH BENIGN FROM MALIGNANT

(71) Applicant: THE JOHNS HOPKINS UNIVERSITY, Baltimore, MD (US)

(72) Inventors: Martha Allen Zeiger, Bethesda, MD (US); Jeanne Kowalski, Baltimore, MD (US); Christopher Umbricht, Towson, MD (US); Yongchun Wang, Towson, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 15/719,815

(22) Filed: Sep. 29, 2017

(65) Prior Publication Data

US 2018/0216192 A1 Aug. 2, 2018

Related U.S. Application Data

(63) Continuation of application No. 15/437,123, filed on Feb. 20, 2017, now abandoned, which is a continuation of application No. 14/964,933, filed on Dec. 10, 2015, now abandoned, which is a continuation of application No. 12/746,418, filed as application No. PCT/US2008/013456 on Dec. 5, 2008, now Pat. No. 9,222,136.

(60) Provisional application No. 61/005,593, filed on Dec. 5, 2007.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/156* (2013.01); *C12Q 2600/158* (2013.01)

(58) Field of Classification Search
None
See application file for complete search history.

(56) References Cited

PUBLICATIONS

Alizadeh, A., et al., "Distinct types of diffuse large B-cell lymphoma identified by gene expression profiling", Nature, (Feb. 3, 2000) vol. 403, pp. 503-511.

Aogi, K., et al., "Telomerase activity in lesions of the thyroid: application to diagnosis of clinical samples including . . . ", Clin. Cancer Res. (1998) vol. 4, pp. 1965-1970.

Aogi, K., et al., "Comparison of telomerase and CD44 expression as diagnostic markers in lesions of the thyroid" Clin. Cancer Res. (1999) vol. 5, pp. 2790-2797.

Baloch, Z., et al., "Follicular-patterned lesions of the thyroid" Am. J. Clin. Pathol. (2002) vol. 117, pp. 143-150.

Baloch, Z., et al., "Diagnosis of follicular neoplasm: a gray zone in thyroid fine-needle aspiration cytology" Diagn. Cytopathol. (2002) vol. 26, No. 1, pp. 41-44.

Brambilla, C., et al., "Oligomer-mediated modulation of hTERT alternative splicing induces telomerase inhibition . . . " Cell. Mol. Life. Sci. (Jul. 2004) vol. 61, pp. 1764-1774.

Brenner, C., et al., "Alternative splicing of the telomerase catalytic subunit in human oocytes and embryos" Mol. Hum. Reprod. (1999) vol. 5, No. 9, pp. 845-850.

Brinkman, B., "Splice variants as cancer biomarkers" Clin. Biochem. (2004) vol. 37, pp. 584-594.

Broccoli, D., et al., "Telomerase activity in normal and malignant hematopoietic cells" Proc. Natl. Acad. Sci. USA (1995) vol. 92, pp. 9082-9086.

Carling, T., et al., "Follicular neoplasms of the thyroid: what to recommend" Thyroid (Jun. 2005) vol. 15, No. 6, pp. 583-587.

Gastro, M., et al., "Thyroid fine-needle aspiration biopsy: progress, practice, and pitfalls" Endocr. Pract. (Mar.-Apr. 2003) vol. 9, No. 2, pp. 128-136.

Cerezo, A., et al., "Constitutive overexpression of human telomerase reverse transcriptase but not c-myc . . . " J. Invest. Dermatol. (Jul. 2003) vol. 121, No. 1, pp. 110-119.

Chen, H., et al., "Papillary carcinoma of the thyroid: can operative management be based solely on fine needle aspiration?" J. Am. Coll. Surg (1997) vol. 184, pp. 605-610.

Cheng, A., et al., "Telomerase activity in benign and malignant human thyroid tissues" Br. J. Cancer, (1998) vol. 77, No. 12, pp. 2177-2180.

Cohen, Y., et al., "Mutational analysis of BRAF in fine needle aspiration biopsies of the thyroid: a potential application . . . " Clin Cancer Res (2004) vol. 10, pp. 2761-2765.

Colgin, L., et al., "The hTERTa splice variant is a dominant negative inhibitor of telomerase activity" Neoplasia (2000) vol. 2, No. 5, pp. 426-432.

(Continued)

*Primary Examiner* — Mindy G Brown
(74) *Attorney, Agent, or Firm* — Johns Hopkins Technology Ventures

(57) ABSTRACT

This invention relates, e.g., to a method for determining if a thyroid tumor in a subject is malignant, comprising determining in a sample from the subject the amount of TERT (telomerase reverse transcriptase) mRNA which lacks the β sequence and the amount of TERT mRNA in the sample which comprises the β sequence, wherein a preponderance (e.g., at least about 55%) of TERT mRNA in the sample which comprises the β sequence indicates that the tumor is malignant, and wherein a preponderance of TERT mRNA which lacks the β sequence indicates that the tumor is not malignant.

9 Claims, 6 Drawing Sheets

Specification includes a Sequence Listing.

(56) References Cited

PUBLICATIONS

Delong, E, et al., "Comparing the areas under two or more correlated receiver operating characteristic curves: a nonparametric . . . ", Biometrics (1988) vol. 44, pp. 837-845.

Fan, Y., et al., "Differential expression of full-length telomerase reverse transcriptase mRNA and telomerase . . . " Clin Cancer Res (Jun. 15, 2005) vol. 11, pp. 4331-4337.

Gallop, R., et al., "Determination and interpretation of the optimal operating point for ROC curves derived through . . . " Understanding Statistics (2003) vol. 2, pp. 219-242.

Geng, Z., et al., "Expression of telomerase hTERT in human non-small cell lung cancer and its . . . " Chin. Med. J. (English) (Oct. 2003) vol. 116, No. 10, pp. 1467-1470.

Gharib, H., et al., "Fine-needle aspiration cytology of the thyroid" Clin. Lab. Med. (1993) vol. 13, No. 3, pp. 699-709.

Gharib, H., et al., "Thyroid nodules: clinical importance, assessment, and treatment" Endocrinol. Metab. Clin. North Am. (2007) vol. 36, pp. 707-735.

Golub, T., et al., "Molecular classification of cancer: class discovery and class prediction by gene expression monitoring" Science (Oct. 15, 1999) vol. 286, pp. 531-537.

Greenberg, R., et al., "Telomerase reverse transcriptase gene is a direct target of c-Myc but is not functionally equivalent . . . " Oncogene (1999) vol. 18, pp. 1219-1226.

Haugen, B., et al., "Telomerase activity in benign and malignant thyroid tumors" Thyroid (1997) vol. 7, No. 3, pp. 337-342.

Hayat, M., et al., "Cancer statistics, trends, and multiple primary cancer analyses from the surveillance, epidemiology . . . " Oncologist (2007) vol. 12, pp. 20-37.

Hisatomi, H., et al., "Expression profile of a γ-deletion variant of the human telomerase reverse transcriptase gene" Neoplasia (May-Jun. 2003) vol. 5, No. 3, pp. 193-197.

Chan, J., et al., "Strict criteria should be applied in the diagnosis of encapsulated follicular variant of papillary . . . " Am. J. Clin. Pathol. (Jan. 2002) vol. 117, pp. 16-18.

Sherman, S., "Why thyroid cancer?" Thyroid (Apr. 1, 2005) vol. 15, No. 4, pp. 303-304.

Venables, J., "Aberrant and alternative splicing in cancer" Cancer Res. (2004) vol. 64, pp. 7647-7654.

Kalnina, Z., et al., "Alterations of pre-mRNA splicing in cancer" Genes Chromosomes Cancer (2005) vol. 42, pp. 342-357.

Kammori, M., et al., "Telomerase activity and telomere length in benign and malignant human thyroid tissues" Cancer Lett. (2000) vol. 159, pp. 175-181.

Kammori, M., et al., "Clinical application of human telomerase reverse transcriptase gene in thyroid . . . " Int. J. Oncol. (May 2003) vol. 22, pp. 985-991.

Kilian, A., et al., "Isolation of a candidate human telomerase catalytic subunit gene, which reveals complex . . . " Hum. Mol. Genet. (1997) vol. 6, No. 12, pp. 2011-2019.

Kim, N., et al., "Specific association of human telomerase activity with immortal cells and cancer" Science (1994) vol. 266, pp. 2011-2015.

Kyo, S., et al., "Sp1 cooperates with c-Myc to activate transcription of the human telomerase reverse . . . " Nucleic Acids Res. (Feb. 1, 2000) vol. 28, No. 3, pp. 669-677.

Liou M. et al., "Human telomerase reverse transcriptase (hTERT) gene expression in FNA samples from . . . " Cancer Lett. (Mar. 10, 2003) vol. 191, pp. 223-227.

Livolsi, V., et al., "The demise of follicular carcinoma of the thyroid gland" Thyroid (1994) vol. 4, No. 2, pp. 233-236.

Lloyd R. et al., "Observer variation in the diagnosis of follicular variant of papillary thyroid carcinoma" Am. J. Sur. Pathol. (2004) vol. 28, pp. 1336-1340.

Lo, C., et al., "Telomerase activity in thyroid malignancy" Thyroid (1999) vol. 9, No. 12, pp. 1215-1220.

Mechanick, J., et al., "Progress in the preoperative diagnosis of thyroid nodules: managing uncertainties and the . . . " Biomed. Pharmacotherapy (2006) vol. 60, pp. 396-404.

Meeker, A., et al., "Telomere length abnormalities occur early in the initiation of epithelial carcinogenesis" Clin. Cancer Res. (May 15, 2004) vol. 10, pp. 3317-3326.

Mora, J., et al., "Telomerase activity in thyroid fine needle aspirates" Acta Cytol. (Nov.-Dec. 2004) vol. 48, No. 6, pp. 818-824.

Nakamura, Y., et al., "Quantitative reevaluation of telomerase activity in cancerous and noncancerous gastrointestinal tissues" Mol. Carcinog. (1999) vol. 26, pp. 312-320.

Onoda, N., et al., "Telomerase activity in thyroid tumors" Oncol. Rep. (1998) vol. 5, pp. 1447-1450.

Ravetto, C., et al., "Usefulness of fine-needle aspiration in the diagnosis of thyroid carcinoma" Cancer (Dec. 25, 2000) vol. 90, No. 6, pp. 357-368.

Renshaw, A., et al., "Why there is the tendency to overdiagnose the follicular variant of papillary thyroid carcinoma" Am. J. Clin. Pathol. (2002) vol. 117, pp. 19-21.

Saji, M., et al., "Human telomerase reverse transcriptase (hTERT) gene expression in thyroid neoplasms" Clin. Cancer Res. (1999) vol. 5, pp. 1483-1489.

Saji, M., et al., "Telomerase activity in the differential diagnosis of papillary carcinoma of the thyroid" Surgery (1997) vol. 122, No. 6, pp. 1137-1140.

Sapio, M., et al., "Detection of BRAF mutation in thyroid papillary carcinomas by mutant allele-specific PCR . . . " Eur. J. Endocrinol. (2006) vol. 154, pp. 341-348.

Sebesta, J., et al., "Does telomerase activity add to the value of fine needle aspirations in evaluating thyroid nodules?" Am. J. Surg. (2001) vol. 181, pp. 420-422.

Segev, D., et al., "Beyond the suspicious thyroid fine needle aspirate" Acta Cytol. (Sep.-Oct. 2003) vol. 47, pp. 709-722.

Siddiqui, M., et al., "Human Telomerase reverse transcriptase expression in diff-quik-stained FNA samples . . . " Diagn. Mol. Pathol. (Jun. 2001) vol. 10, No. 2, pp. 123-129.

Skotheim, R., et al., "Alternative splicing in cancer: noise, functional, or systematic?" Int. J. Biochem. Cell Biol. (2007) vol. 39, pp. 1432-1449.

Suzuki, S., et al., "New attempt of preoperative differential diagnosis of thyroid neoplasms by telomerase activity measurement" Oncol. Rep. (2002) vol. 9, pp. 539-544.

Tahara, H., et al., "Immuno-histochemical detection of human telomerase catalytic component, hTERT, in human colorectal tumor . . . " Oncogene (1999) vol. 18, pp. 1561-1567.

Trulsson, L., et al., "Telomerase activity in surgical specimens and fine-needle aspiration biopsies from hyperplastic . . . " Am. J. Surg. (Jul. 2003) vol. 186, pp. 83-88.

Udelsman, R., et al., "Randomized prospective evaluation of frozen-section analysis for follicular neoplasms of the thyroid" Ann. Surg. (2001) vol. 233, No. 6, pp. 716-722.

Ulaner G., et al., "Telomerase activity in human development is regulated by human telomerase reverse transcriptase (hTERT) . . . " Cancer Res. (1998) vol. 58, pp. 4168-4172.

Ulaner, G., et al., "Regulation of telomerase by alternate splicing of human telomerase reverse transcriptase ((hTERT) in normal . . . " Int. J. Cancer (2000) vol. 85, pp. 330-335.

Umbricht, C., et al., "Telomerase activity: a marker to distinguish follicular thyroid adenoma from carcinoma" Cancer Res. (1997) vol. 57, pp. 2144-2147.

Umbricht, C., et al., "Human telomerase reverse transcriptase gene expression and the surgical management . . . " Clin. Cancer Res. (Sep. 1, 2004) vol. 10, pp. 5762-5768.

Van T Veer, L., et al., "Gene expression profiling predicts clinical outcome of breast cancer" Nature (Jan. 31, 2002) vol. 415, pp. 530-536.

Wick, M., et al., "Genomic organization and promoter characterization of the gene encoding the human telomerase reverse . . . " Gene (1999) vol. 232, pp. 97-106.

Wu, K., et al., "Direct activation of TERT transcription by c-MYC" Nature Genetics (1999) vol. 21, pp. 220-224.

Yashima, K., et al., "Telomerase activity in benign and malignant thyroid diseases" Surgery (1997) vol. 122, pp. 1141-1146.

Yi, X., et al., "An alternate splicing variant of the human telomerase catalytic subunit inhibits telomerase activity" Neoplasia (2000) vol. 2, No. 5, pp. 433-440.

(56) References Cited

PUBLICATIONS

Yi, X., et al., "Quantitation of telomerase components and hTERT mRNA splicing patterns in immortal human cells" Nucleic Acids Res. (2001) vol. 29, No. 23, pp. 4818-4825.

Yoder, B., et al., "Validation of a five-tier cytodiagnostic system for thyroid fine needle aspiration biopsies using . . . " Thyroid (2006) vol. 16, No. 8, pp. 781-786.

Yokoyama, Y., et al., "Alternatively spliced variant deleting exons 7 and 8 of the human telomerase reverse . . . " Mol. Hum. Reprod. (2001) vol. 7, No. 9, pp. 853-857.

Zaffaroni N., et al., "Transcription and alternative splicing of telomerase reverse transcriptase in benign and malignant . . . " J. Pathol. (Sep. 2002) vol. 198, pp. 37-46.

Zeiger, M., et al., "Follicular thyroid lesions, elements that affect both diagnosis and prognosis" J. Surg. Oncol. (Mar. 1, 2005) vol. 89, pp. 108-113.

Zeiger, M., et al., "Human telomerase reverse transcriptase (hTERT) gene expression in FNA samples from . . . " Surgery (1999) vol. 126, No. 6, pp. 1195-1199.

Zou, L., et al., "Transcript regulation of human telomerase reverse transcriptase by c-myc . . . " Acta Biochim. Biophys. Sin. (Shanghai) (Jan. 2005) vol. 37, No. 1, pp. 32-38.

Hoang-Vu, et al., "Expression of telomerase genes in thyroid carcinoma" International Journal of Oncology (2002) vol. 21, pp. 265-272.

Yasuhiro Ito, et al., "Telomerase activity in thyroid neoplasms evaluated by the expression of human telomerase reverse transcriptase (hTERT)" Anticancer Research (2005) vol. 25, pp. 509-514.

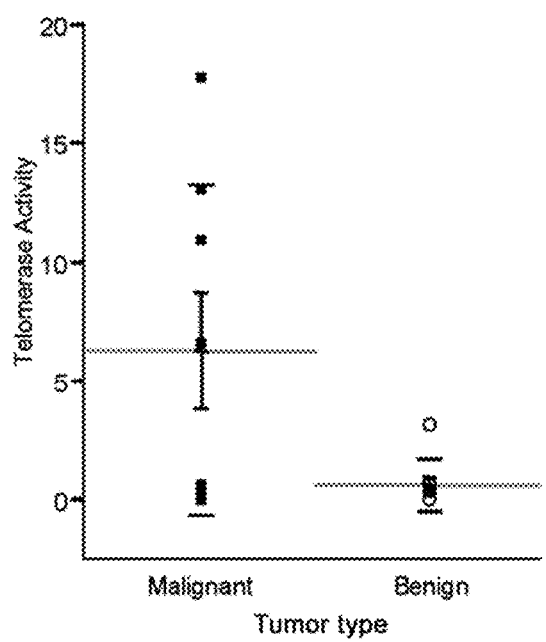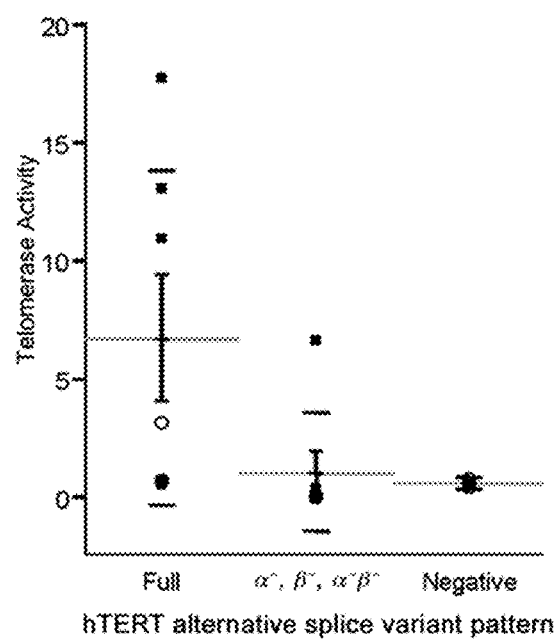

ALTERNATIVE SPLICE VARIANT PATTERNS OF HUMAN TELOMERASE REVERSE TRANSCRIPTASE (HTERT) IN THYROID TUMORS TO DISTINGUISH BENIGN FROM MALIGNANT

CROSS-REFERENCE TO RELATED APPLICATIONS

This application is a Continuation of U.S. patent application Ser. No. 15/437,123, filed Feb. 20, 2017, which is a Continuation of U.S. patent application Ser. No. 14/964,933, filed Dec. 10, 2015, which is a Continuation of U.S. patent application Ser. No. 12/746,418, filed Jun. 4, 2010, now U.S. Pat. No. 9,222,136 granted on Dec. 29, 2015, which is a 35 U.S.C. § 371 U.S. national entry of International Application PCT/US2008/013456, having an international filing date of Dec. 5, 2008, which claims the benefit of U.S. Provisional Application No. 61/005,593, filed Dec. 5, 2007, the content of each of the aforementioned applications is herein incorporated by reference in their entirety.

STATEMENT OF GOVERNMENTAL INTEREST

This invention was made with government support under grant no. CA095703, awarded by the National Institutes of Health. The government has certain rights in the invention.

BACKGROUND INFORMATION

The clinical problem associated with patients who present with a suspicious thyroid nodule continues to place clinicians and patients in situations where decisions about the surgical approach need to be made with inadequate information. Although fine needle aspiration (FNA) biopsy of a thyroid nodule is very sensitive in the detection of malignancy, it is indeterminate or suspicious in 20-30% of cases. There are over 100,000 patients each year who present with a suspicious thyroid nodule in the United States. Terminologies commonly used in suspicious cytopathology reports include the following: follicular or Hürthle cell neoplasm, suspicious for papillary or follicular variant of papillary thyroid cancer, or cellular atypia. Because clinicians often cannot determine malignancy, either pre- or intra-operatively, patients with suspicious thyroid lesions cannot be optimally managed. This often results in two scenarios: 1) patients who ultimately have a benign lesion on final histopathology may be subjected to unnecessary surgery; 2) patients with a malignant thyroid nodule may need to undergo a second operation for completion thyroidectomy only after a diagnosis of cancer is rendered on permanent histological section. Thus, there is a need for a diagnostic test that can distinguish more effectively between malignant and non-malignant thyroid tumors, and that can provide guidance as to whether aggressive treatment, such as a total thyroidectomy, should be administered.

Telomerase is a ribonucleoprotein complex that stabilizes linear chromosomes (e.g. human chromosomes) by adding telomere sequence (TTAGGG) repeats to their ends. The protein component of this complex, the telomerase reverse transcriptase catalytic subunit (TERT), has been characterized in a variety of species. The human form of the protein is designated as hTERT (human telomerase reverse transcriptase). The wild type hTERT mRNA contains 16 exons. In addition, alternative splicing of RNA transcribed from the hTERT DNA has been observed. Seven alternative splice sites have been reported for hTERT, giving rise to splice variants that may include three deletions and four insertions. See, e.g., J P Venables (2004) Cancer Res 64, 7647-7654; Kilian et al, (1997) Hum Mol Genet 6, 2011-2019; Killin et al., U.S. Pat. No. 6,916,642). The splicing patterns are presented schematically in FIGS. 1A and 1B herein. There are several possible combinations of these alternative splice sites resulting in a large number of potential variant transcripts, but only a few have been confirmed (Hisatomi et al. (2003) Neoplasia 5, 193-197). The sequence of the wild type hTERT mRNA, as used herein, is represented by SEQ ID NO:1 (taken from U.S. Pat. No. 6,916,642). Variants of this sequence, including updated sequences, polymorphisms, allelic variants, or the like, are also included. The numbering of the sequence of SEQ ID NO:1 is used herein to indicate the location of the splice sites. The sequence of the polypeptide translated from SEQ ID NO:1 is represented by SEQ ID NO:2.

The four insertions and one deletion (β-deletion, 182 nt) generated by the alternative splices result in premature termination and non-functional proteins (Hisatomi et al. (2003) (supra)). The β-deletion, in which exons 7 and 8 are deleted, at nucleotides (nt) 2286-2468, gives rise to a reading frame-shift at nucleotide 2287, which is joined to nucleotide 2469, and a subsequent termination codon at nucleotide 2605. The hTERT protein translated from this alternatively spliced mRNA is thus truncated. The 182 nt deleted β sequence (sometimes referred to herein as the β-deletion) is represented by SEQ ID NO:3; the protein sequence translated from it is inactive and is represented by SEQ ID NO:4. The translation product of an mRNA having the α-splice (36 bp deleted within the RT motif A, extending from nt 2131-2166) has been shown in cell culture studies to be a dominant negative inhibitor of telomerase activity (Wick et al. (1999) Gene 232, 97-106). The sequence of this α-deletion (sometimes referred to herein as the α-sequence) is represented by SEQ ID NO:5; the polypeptide translated from it is represented by SEQ ID NO:6. The γ-deletion (189 bp) has been identified in hepatocellular carcinoma cell lines and is also believed to be non-functional (Kilian et al, (1997) (supra)).

Telomerase enzyme activity has been reported by several groups to be regulated by posttranscriptional alternative splicing of hTERT (See, e.g., Colgin et al. (2000) Neoplasia 2, 426-432; Fan et al. (2005) Clin Cancer Res 11, 4331-4337). Furthermore, the patterns of hTERT alternative splice variants are known to vary in ovary, kidney, uterine and breast cancer, compared to corresponding adjacent normal tissues (See, e.g., Colgin et al. (2000) (supra); Ulaner et al. (1998) Cancer Res 58, 4168-4172; Ulaner et al. (2000) Int J Cancer 85, 330-335; Yokoyama et al. (2001) Mol Hum Reprod 7, 853-857). To our knowledge, no studies have reported differences between alternative splice variant patterns in benign and malignant tumors that originate from the same tissue type, or splice variant patterns that are more specific markers of malignant or benign disease than overall hTERT transcript levels. Comparable TERT alternative splicing patterns, including the α and the β deletions, have been characterized from vertebrate species other than human; the precise locations of the splice sites and the sequences of the wild type transcript are readily available to a skilled worker.

DESCRIPTION OF THE DRAWINGS

FIG. 1A shows the structure of hTERT deletion variants. Locations of telomerase-specific T motif, 7 conserved reverse transcriptase (RT) motifs (1, 2, A, B', C, D, and E), exons 3-13, and deletion sites are indicated. In FIG. 1B, the alternative splice sites (α-, β-, γ-) are depicted with the respective resulting transcripts. Primers F1720 and R3071 were used for the first PCR reaction. Nested primers F2162 and R2580 were used to amplify the region containing the α- and β-deletions, resulting in four possible PCR products. Nested primers F2653 and R2932 were used to amplify the region containing the γ-deletion, resulting two possible PCR products.

FIG. 2A shows gels demonstrating hTERT alternative splice variant patterns present in representative thyroid tumors. The one blank lane in FA represents an hTERT negative tumor. FIG. 2B shows plots of relative proportions of full-length (F), α-deletion and β-/α-β-deletion transcripts for the 8 thyroid tumor types (only tumor types that exhibited the combination of α-β-deletion are labeled β-/α-β-). AN, adenomatoid nodule; FA, follicular adenoma; FC, follicular carcinoma; FVPTC, follicular variant of papillary thyroid carcinoma; HA, Hüthle cell adenoma; HC, Hüthle cell carcinoma; LcT, lymphocytic thyroiditis nodule; PTC, papillary thyroid carcinoma.

FIG. 3A-3B shows telomerase enzyme activity in a subset of 16 thyroid tumors. FIG. 3A shows telomerase activity found in benign vs. malignant tumors. FIG. 3B shows telomerase activity found in tumors with different hTERT splice patterns, full-length, α-, β-/α-β- or hTERT negative. Results are plotted in arbitrary units. The long horizontal bars indicate means; vertical bars, the standard error of the means; and the short horizontal bars, standard deviations. (v), malignant tumors; (O), benign tumors.

DESCRIPTION OF THE INVENTION

Figure 1A:
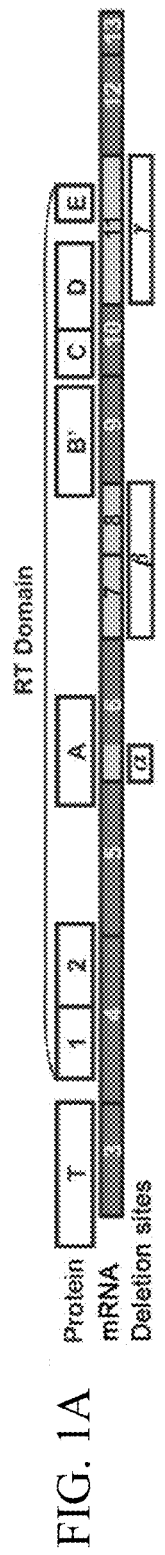
FIG. 1A-1B shows a diagram of hTERT alternative splice variants.

The present inventors show herein that an hTERT mRNA alternative splice variant in which the 182 nucleotide (nt) sequence from nt 2286-nt 2468 (the β sequence) has been deleted is disproportionately present in thyroid tumors that are non-malignant, whereas the presence of the β sequence in an hTERT mRNA is characteristic of thyroid tumors that are malignant. This 182 bβ sequence (sometimes referred to herein as the β-deletion or the β-sequence) is represented as SEQ ID NO:3. [As used herein, the term "a TERT mRNA" (e.g., an hTERT mRNA) refers to an mRNA that has been transcribed from a TERT gene (e.g., an hTERT gene). A TERT mRNA can be one of the wild type spliced mRNAs, or it can be an alternatively spliced variant (sometimes referred to herein as an ASV).] This observation by the inventors provides the basis for an assay to determine if a thyroid tumor in a subject is malignant; the different types of RNAs (or proteins encoded by them) can serve as diagnostic markers for whether a thyroid tumor is malignant or benign. An assay of the invention can be used, e.g., to classify a thyroid tumor as being malignant or benign, to monitor the response to a treatment of a thyroid tumor, to identify an agent for treating a thyroid tumor, or other applications which will be evident to a skilled worker.

Additional spliced mRNAs from other genes, whose presence or absence is diagnostic of malignant thyroid tumors, are also disclosed.

Advantages of a method of the invention include that it is rapid, inexpensive, and accurate. The differential diagnosis of a thyroid tumor can, e.g., prevent a subject having a benign tumor from having to undergo unnecessary surgery, and can allow for a subject found to have a malignant tumor to undergo only a single operation (a total thyroidectomy) to remove the entire thyroid. This is particularly true in the case in which prior screening by standard cytological analysis of a fine needle aspirate (FNA) has classified the tumor as being "indeterminate," "suspicious," or "inadequate."

One aspect of the invention is a method for determining if a thyroid tumor in a subject is malignant, comprising determining in a sample from the subject the amount of TERT (telomerase reverse transcriptase) mRNA which lacks the β sequence and the amount of TERT mRNA in the sample which comprises the β sequence, wherein a preponderance (e.g., at least about 55%) of TERT mRNA in the sample which comprises the β sequence indicates that the tumor is malignant (likely to be malignant), and whereas a preponderance (e.g., at least about 55%) of hTERT mRNA which lacks the β sequence indicates that the tumor is not malignant (likely not to be malignant).

In one embodiment of this method, the subject is human; the TERT mRNA is hTERT mRNA; and the β sequence is the 182 bβ sequence represented by SEQ ID NO:3.

In one embodiment, a ratio of at least about 0.55 (e.g., at least about 0.59) of the amount of hTERT mRNA which contains the sequence of SEQ ID NO:3 compared to the total amount of hTERT mRNA which either contains or which lacks the sequence of SEQ ID NO:3 indicates that the tumor is malignant; and a ratio of at least about 0.55 (e.g., at least about 0.59) of the amount of hTERT mRNA which lacks the sequence of SEQ ID NO:3 compared to the total amount of hTERT mRNA which contains or which lacks the sequence of SEQ ID NO:3 indicates that the tumor is not malignant.

In another embodiment, the method further comprises determining the amount of mRNA which lacks the α sequence (represented by SEQ ID NO:5) and/or the amount of mRNA which lacks both the α sequence and the β sequence are determined; wherein, a ratio of the amount of hTERT mRNA which contains the sequence of SEQ ID NO:3 compared to the total amount of
  hTERT mRNA which contains the sequence of SEQ ID NO:3, and
  hTERT mRNA which lacks the sequence of SEQ ID NO:3, and
  hTERT mRNA which lacks the α sequence (SEQ ID NO:5) and/or which lacks both SEQ ID NO:3 and SEQ ID NO:5)
of at least about 0.55 (e.g., at least about 0.59) indicates that the tumor is malignant, and a ratio of the amount of hTERT mRNA which lacks the sequence of SEQ ID NO:3 compared to the total amount of
  hTERT mRNA which contains the sequence of SEQ ID NO:3, and
  hTERT mRNA which lacks the sequence of SEQ ID NO:3, and
  hTERT mRNA which lacks the α sequence (SEQ ID NO:5) and/or which lacks both SEQ ID NO:3 and SEQ ID NO:5
of at least about 0.55 (e.g., at least about 0.59) indicates that the tumor is not malignant.

In one aspect of the invention, the amount of each of the TERT mRNAs is determined by a method comprising amplifying mRNA in the sample by reverse transcriptase polymerase chain reaction (RT-PCR), using suitable PCR primers to amplify each mRNA species of interest; and detecting the amounts of the amplified products. The amounts of the amplified products can be measured by a method comprising (a) subjecting the amplified products to a sizing procedure and categorizing the amplified products on the basis of their size; and/or (b) hybridizing the amplified products to suitable nucleic acid probes which are specific for the β-sequence or for a control sequence that is present in TERT mRNAs which either comprise, or lack, the β-sequence.

In another aspect of the invention, the amount of each of the TERT mRNAs is determined by a method comprising quantitative real time PCR.

In another aspect of the invention, wherein the sample is a tissue sample or a fine needle aspirate (FNA), wherein the amount of each of the hTERT mRNAs is determined by a method that comprises performing in situ hybridization of the sample with suitable probes that are specific for the β-sequence, or that are specific for a control sequence that is present in TERT mRNAs which either comprise, or lack, the β-sequence.

In another aspect of the invention, the amount of each of the hTERT mRNAs is determined by a method that comprises measuring the amounts of polypeptides translated from each of the mRNAs. For example, the polypeptides can be measured by reacting them with antibodies that are specific for epitopes within the β-sequence or that are specific for control epitopes that are present in polypeptides translated from TERT mRNAs which either comprise, or lack, the β-sequence.

A method as above can further comprise: (a) analyzing the sample for the presence of a BRAF mutation, wherein the presence of the mutation is further indicative that the tumor is malignant; and/or (b) determining the level of expression in the sample of one or more of the genes HMGA2, PLAG1, CDH3, SPOCK1, CEACAM6, DPP4, PRSS3, PDESA, LRRK2, RAG2, AGTR1 or TP05, compared to the level in a benign tumor, wherein a statistically significant amount of over-expression of one of more of genes HMGA2, PLAG1, CDH3, SPOCK1, CEACAM6, DPP4, PRSS3, PDESA or LRRK2 further indicates that the tumor is malignant, and a statistically significant amount of under-expression of one or more of RAG2, AGTR1 or TP05 further indicates that the tumor is not malignant; and/or (c) determining the level of the spliced RNA species listed in Tables 3 and 4, compared to the level in a benign tumor, wherein a significantly increased amount of one or more of the spliced species in Table 3 further indicates that the tumor is malignant, or a significantly increased amount of one of more of the spliced species in Table 4 indicates that the tumor is benign. The level of expression of the proteins can be determined by measuring the amount of mRNA transcribed from the genes, or the amount of protein translated from the mRNA.

A method as above can further comprise, if the tumor is determined to be malignant, performing a total thyroidectomy on the subject, or, if the tumor is determined not to be malignant, not performing a total thyroidectomy on the subject. A method of the invention can be a method for deciding on a treatment modality: if a tumor is determined to be malignant, a decision is made to perform a total thyroidectomy on the subject, but if a tumor is determined not to be malignant, a decision is made not to perform a total thyroidectomy on the subject.

One aspect of the invention is a method for treating a subject having a thyroid tumor, comprising determining by a method of the invention whether the tumor is malignant and, if the tumor is malignant, treating the subject aggressively for thyroid cancer, and if the tumor is determined not to be malignant, not treating the subject aggressively for thyroid cancer.

In one aspect of the invention, the method is carried out both before or at approximately the same time as, and after, the administration of a treatment for thyroid cancer, and is a method for determining the effectiveness of the treatment.

This invention relates, e.g., to a method for determining if a thyroid tumor in a subject is malignant, comprising measuring in a sample from the subject the amounts, compared to a baseline value, or compared to each other, of wild type transcripts and/or splice variant transcripts of the telomerase reverse transcriptase (TERT) gene and/or one or more of the of the genes listed in Tables 3 and 4, wherein the amount of the transcript(s) compared to the baseline value (or compared to each other) indicates whether the tumor is malignant or benign. The baseline value can be any value that reflects the difference between the expression of the transcript(s) in a malignant tumor compared to a non-malignant (benign) tumor. The TERT gene can be from any vertebrate, including a human. Although much of the discussion herein is directed to human subjects (e.g., patients) and human telomerase reverse transcriptase (hTERT), it will be evident to a skilled worker that non-human subjects, and other forms of TERT, are also included.

By a "sample" (e.g. a test sample) from a subject having a thyroid tumor is meant a sample that is suspected of comprising malignant thyroid tumor cells. The sample may be, e.g., from a biopsy of a thyroid tumor (e.g., a fine needle aspirate, or FNA). Furthermore, it is expected that, like most cancers, tumor cells from the thyroid are shed into the blood stream. Therefore, blood samples (e.g., plasma or serum) can be assayed by a method of the invention. Lymph node samples (e.g., FNAs) can also be assayed.

Methods for obtaining samples and preparing them for analysis (e.g., for detection of the amount of an mRNA or of a protein translated from the mRNA) are conventional and well-known in the art.

A "subject," as used herein, includes any vertebrate that has a thyroid tumor. Suitable subjects (patients) include laboratory animals (e.g., mouse, rat, rabbit, monkey, or guinea pig), farm animals (e.g., cattle, horses, pigs, sheep, goats, etc.), and domestic animals or pets (e.g., cats or dogs). Non-human primates and, preferably, humans, are included.

One embodiment of the invention is a method for determining if a thyroid tumor in a subject (e.g., a human subject) is malignant, comprising measuring in a sample from the subject the amount of TERT (e.g., for a human subject, hTERT) mRNA which lacks the β-sequence, and the amount of TERT mRNA which contains the β-sequence, and determining from the relative amounts of the mRNA lacking or having the β-sequence whether the tumor is malignant. A preponderance (e.g., at least about 55%, or at least about 59%) of TERT mRNA in the sample that comprises the β-sequence indicates that the tumor is malignant, whereas a preponderance (e.g., at least about 55%, or at least about 59%) of TERT mRNA in the sample which lacks the β-sequence indicates that the tumor is not malignant (is benign).

"About," as used herein, refers to plus or minus 10%. Thus, "about" 55% includes 49.5%-60.5%, so a lower limit of "at least about 55%" includes at least 49.5%; and "about"

59% includes 53.1%-64.9%, so a lower limit of "at least about 59%" includes at least 53%. "About" also refers to plus of minus 10% when referring to lengths of polynucleotides or polypeptides. When a value is non-divisible, such as the number of nucleotides or amino acids, and the value is not an integer, it will be evident to a skilled worker that the nearest integer is meant.

Because assays in the biomedical field are rarely 100% accurate, as used herein an assay that indicates that a tumor is malignant indicates that the tumor is likely to be malignant. That is, the tumor has at least about a 70% chance (e.g., at least about an 80% or a 90% chance) of being malignant. For example, as is shown in the Examples, a ratio greater than about 0.55 (e.g., greater than about 0.59) of hTERT mRNA having the β-sequence, compared to the total amount of hTERT mRNA (having or not having this sequence) provides a specificity of 90%, indicating that the presence of such a ratio suggests that a tumor has at least about a 90% chance of being malignant.

In one embodiment of the invention, the amount of TERT mRNA (e.g., in the case of humans, hTERT mRNA) which lacks the β-sequence (e.g., in humans, SEQ ID NO:3) is compared to the sum of hTERT transcripts in the sample which do and do not include the (3-sequence, wherein a preponderance (e.g., at least about 55%) of TERT transcripts which contain the β-sequence indicates that the tumor is malignant, whereas a preponderance (e.g., at least about 55%%) of TERT transcripts which lack the β-sequence indicates that the tumor is not malignant.

In another embodiment, the amount of an mRNA or interest (either comprising or lacking the β-sequence) is compared to the amounts of one or more of the following types of mRNA molecules: mRNAs having the α-deletion, and/or having the β-deletion, and/or having both the α-deletion and the β-deletion, and/or having neither of these deletions. For example, the amount of an mRNA of interest can be compared to the total amount of all four of these types of mRNA.

Instead of, or in addition to, comparing a TERT mRNA of interest to the total amounts of TERT mRNA within a given sample which comprise, or lack, the β-sequence, one can compare the amount of the mRNA of interest to the amount of a control mRNA within the sample. For example, one can normalize the amount of a TERT mRNA of interest to a constitutively produced mRNA, such as actin, tubulin, or the like. Consider now a hypothetical example, in which the amount of n-spliced TERT mRNA in a test sample, as normalized to such an internal control, is compared to the amount of n-spliced TERT mRNA, normalized to a comparable control, from a pool of thyroid tumors or cells in culture which are known to be benign or known to be malignant. The values from the pool of tumors or cells may be available in a database compiled from the values, and/or they may be determined based on published data or on retrospective studies of patients' tissues, and other information as would be apparent to a person of ordinary skill implementing a method of the invention. Because it can be difficult to use actual patient samples in a clinical environment, reference standards, such as RNA (or DNA) produced in vitro (e.g., recombinantly), or defined amounts of a purified or semi-purified RNA (or DNA) can be used. The normalized amount of n-spliced TERT mRNA representing the level in a benign tumor, or the normalized amount of n-spliced TERT mRNA representing the level in a in a malignant tumor, can serve as a baseline value. Upper and lower baseline values (reference standards) can be used. Baseline values may be selected using statistical tools that provide an appropriate confidence interval so that measured levels that fall outside the standard value can be accepted as being aberrant from a diagnostic perspective, and predictive of the presence (or absence) of malignancy.

In the hypothetical example above, consider the case in which the amount of n-spliced mRNA in the test sample is statistically the same (or higher) than the baseline value corresponding to benign thyroid tumors. This indicates that the tumor is likely to be benign. However, if the amount of the n-spliced mRNA in the test sample is statistically significantly lower than this baseline value, this indicates that the test tumor is likely to be malignant. Alternatively, a baseline value can be determined on the basis of a subject, population of subjects, etc., which are known to have malignant thyroid tumors. In this case, if the amount of n-spliced mRNA in a test sample is statistically the same (or lower) than the baseline value corresponding to malignant thyroid tumors, then the test tumor is likely to be malignant. However, if the amount of the n-spliced mRNA in the test sample is statistically significantly higher than the baseline value, the test tumor is likely to be benign.

A "significant" increase or decrease in the amount of an mRNA or protein, as used herein, can refer to a difference which is reproducible or statistically significant, as determined using statistical methods that are appropriate and well-known in the art, generally with a probability value of less than five percent chance of the change being due to random variation. Some such statistical tests will be evident to a skilled worker, and some are discussed in the Example herein. For example, a significant increase in the amount of mRNA or protein compared to a baseline value can be at least about 50% higher (e.g., at least about 2-fold, 5-fold, 10-fold, or more higher).

In one embodiment of the invention, the thyroid tumor being tested is suspected of being malignant. For example, the thyroid tumor can have been classified as being suspicious (for malignancy) or as being indeterminate, based on a cytological assay, such as a cytological assay performed on a sample obtained from a fine needle aspirate (FNA). For discussions of what criteria are used to categorize a thyroid tumor as suspicious or indeterminate, and the methods for carrying out a FNA cytological assay, see, e.g., Banks et al. (2008) *Thyroid* 18, 933-941; Baloch et al. (2002) *Diag Cytopathol* 26, 41-44; or Yoder et al. (2006) *Thyroid* 16, 781-786.

A variety of methods can be employed to determine the amounts of the TERT mRNA species in a sample.

In one embodiment of the invention, the amount of an mRNA of a given type (such as a particular splice variant of interest) is measured directly, without further amplification. For example, the presence of a splice or the length of an mRNA can be determined by Northern analysis, a probe protection assay, mass spectroscopy, or other conventional methods. Appropriate probes for such methods will be evident to a skilled worker. For example, for an RNAse probe protection assay to distinguish a wild type hTERT mRNA from a TERT mRNA having a particular splice variant, the probe can be a DNA fragment having sequences corresponding to the junction of the wild type (non-deleted) sequence and the alternative intron/exon sequence or derived from the sequence surrounding the alternative intron/exon deletion site. For example, a DNA fragment consisting of sequences of the wild type hTERT mRNA that span nucleotides 2286-2287 (e.g., a fragment consisting of nucleotides 2236-2336) will protect the wild type mRNA sequence as a 101 nt fragment, but will protect an RNA with the n-splice as a 51 nt fragment. Fragments for RNAse probe protection are usually chosen in the range of 30 to 400 bases and are positioned to yield readily distinguishable protection products.

In another embodiment of the invention, the amounts of the mRNAs are determined indirectly, by a method comprising reverse transcribing them into cDNAs; amplifying the cDNAs by any of a variety of suitable methods, using suitable primers; and detecting the amounts of the amplified product(s). Among the well-known amplification methods that can be used are, e.g., the polymerase chain reaction (PCR) which, when carried out in conjunction with the reverse transcriptase step is sometimes referred to as RT-PCR, quantitative or semi-quantitative real time PCR, ligase chain reaction DNA signal amplification, amplifiable RNA reporters, Q-beta replication, transcription-based amplification, boomerang DNA amplification, strand displacement activation, cycling probe technology, isothermal nucleic acid sequence based amplification, or other self-sustained sequence replication assays.

For amplification assays, primer pairs can be used that either flank the alternative intron/exons or require the presence of the alternative intron/exon for amplification. Suitable primers can be designed based on the sequences presented herein, in view of the known splice site positions. Generally, the primer pairs are designed to generate an amplification product of an easily detectable size. The primers may only allow amplification of a single alternative intron/exon. For example, at least one primer of a primer pair may be specific for a sequence within the 182 nt β-sequence. If the second primer of the primer pair is also specific for a sequence in the β-sequence, then only TERT mRNAs that comprise this sequence will be amplified. Similarly, if the second primer lies 5' or 3' to the first primer, only TERT mRNAs that comprise the β-sequence will be amplified. In another embodiment, two primers flanking the β-sequence can be used, and the size of the resulting amplification product will indicate if the β-sequence is present or absent. In another embodiment, at least one primer of a primer pair is specific for a sequence that spans the intron/exon junction of an alternative splice site (e.g., that spans nucleotides 2286-2287, such as a primer comprising nucleotides 2276-2296). In this case, only RNAs that are not spliced at this site will be amplified.

In some circumstances, detection of multiple alternative intron/exons, and/or wild type intron/exons, in the same RNA preparation, may be carried out. For example, it may be useful to amplify a sequence that contains both the β-sequence (if present) and a nearby sequence that is present in hTERT mRNAs that either comprise the β-sequence or lack this sequence. Nearby sequences can be amplified, e.g., by a forward primer that lies 5' to the 5' end of the β-sequence, and/or a reverse primer that binds to a sequence in exon 9 or 10. Amplification of the nearby sequences can be used to determine if an mRNA lacking the β-sequence is present in the sample being tested. Alternatively, separate, control primer pairs can be used to amplify either the β-sequence (if present) or a control sequence that is present in TERT mRNAs that either do or do not comprise the β-sequence. In some embodiments, a longer TERT mRNA is first amplified, and then nested primers are used to amplify sequences within the first amplification product. A typical such set of nested amplifications is described in the Examples herein. Other suitable combinations of broader plus nested amplification reactions will be evident to a skilled worker.

Suitable amplification primers (e.g., pairs of PCR primers) can be designed by conventional methods. If desired, conventional software programs can be employed to aid in designing the primers. Oligonucleotides used as amplification primers (e.g., DNA, RNA, PNA, LNA, or the like) preferably do not have self-complementary sequences or have complementary sequences at their 3' end (to prevent primer-dimer formation). Preferably, the primers have a GC content of about 50% and may contain restriction sites to facilitate cloning. Amplification primers can be between about 10 and about 100 nt in length. They are generally at least about 15 nt and not longer than 50 nt, although in some circumstances and conditions shorter or longer lengths can be used. For example, primers from between about 15 and about 35 nucleotides can be used. Amplification primers can be purchased commercially from a variety of sources, or can be chemically synthesized, using conventional procedures. Some exemplary PCR primers that can be used to detect spliced variants of hTERT are described, e.g., in the Examples herein, as well as in Stein Saeboe-Larssen et al. (2006) *BMC Molecular Biology* 7, 26; Kilian et al, (1997) *Hum Mol Genet* 6, 2011-2019; and Killin et al., U.S. Pat. No. 6,916,642.

PCR primers are annealed to cDNA and sufficient amplification cycles, generally about 20-40 cycles, are performed to yield a product that is readily detected, e.g. by gel electrophoresis and staining. Methods of PCR amplification, and reagents used therein, are conventional. For guidance, see, e.g., PCR Protocols: A Guide to Methods and Applications (Innis et al. eds, Academic Press Inc. San Diego, Calif. (1990)). These and other molecular biology methods used in methods of the invention are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

If desired, a detectable label, such as a radiolabel, biotinylated label, fluorphor, chemiluminescent label, or the like, may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Another method for detecting mRNAs utilizes quantitative (or semi-quantitative) real-time PCR, using, for example, molecular beacons or FRET (fluorescence resonance energy transfer). The FRET technique utilizes molecules having a combination of fluorescent labels which, when in proximity to one another, allows for the transfer of energy between labels. See, e.g., the Examples herein or "iQ5 Real Time PCR Detection System" Manual (Bio-Rad, Hercules, Calif.).

The presence and amounts of the individual amplification products can be determined by a variety of procedures, including sizing them (e.g., by gel electrophoresis, capillary electrophoresis, Southern blot analysis, sequencing, high performance liquid chromatography, mass spectroscopy, etc.)

Alternatively, or in conjunction with a sizing procedure, the amplified DNA products can be hybridized to suitable detectable nucleic acid probes, which are specific for one or more sequences that are present (or absent) in an mRNA of interest.

Probes for hybridization are generally at least about 15, 20, or 25 nucleotides, but may range from about 10 to a full-length sequence. The probes may comprise additional sequences that do not hybridize to a DNA or an mRNA (or portion thereof) of interest. Probes are generally DNA, but may be RNA, PNA, LNA or derivatives thereof. Hybridization probes may be labeled with a radiolabel, chemiluminescent label, or any of the myriad other known labels, such as those discussed above in relation to amplification primers. Electrochemiluminescence or laser-induced fluorescence may be used.

For example, to detect the presence or absence of the β-sequence, the amplified products can be hybridized to a probe comprising at least about 10 (e.g., at least 15, 20, 25, 30, 35, 40 or as many as all) contiguous nucleotides of the β sequence (SEQ ID NO:3), or to complete complements thereof, under conditions in which the hybridization is specific. As technology improves, it may be possible to utilize probes that are even shorter than 10 nts. If desired, a control probe can be used which is specific for a sequence that is present in all TERT transcripts, such as a sequence from the exon 4, 5, 9 or 10 region. For example, an amplified DNA product can be hybridized to a sequence specific for the β region and to a control sequence from elsewhere within the TERT transcript. A DNA to which the TERT control as well as the β probe hybridize reflects a TERT RNA that comprises the β sequence, whereas a DNA to which the TERT control but not the β probe hybridizes, reflects a TERT RNA that lacks the β sequence. Other suitable internal hybridization controls will be evident to a skilled worker.

Probes and conditions are selected, using routine conventional procedures, to insure that hybridization of a probe to a sequence of interest is specific. Methods for designing nucleic acid probes that are specific for a nucleic acid of interest are conventional and well known in the art. The TERT nucleic acid sequences disclosed herein, in combination with the splice maps, can be used to design probes that are specific for any splice variant of interest.

A probe that is "specific for" a nucleic acid (e.g., an mRNA or a cDNA) contains sequences that are substantially similar to (e.g., hybridize under conditions of high stringency to) one of the strands of the nucleic acid. By hybridizing "specifically" is meant herein that the two components (the mRNA or cDNA and the nucleic acid probe) bind selectively to each other and not generally to other components unintended for binding to the subject components. The parameters required to achieve specific binding can be determined routinely, using conventional methods in the art. Probes that bind specifically to a target of interest do not necessarily have to be completely complementary to them. For example, a probe can be at least about 95% identical to the target, provided that the probe binds specifically to the target under defined hybridization conditions, such a conditions of high stringency.

As used herein, "conditions of high stringency" or "high stringent hybridization conditions" means any conditions in which hybridization will occur when there is at least about 95%, preferably about 97 to 100%, nucleotide complementarity (identity) between a nucleic acid of interest and a probe. Generally, high stringency conditions are selected to be about 5° C. to 20° C. lower than the thermal melting point ($T_m$) for the specific sequence at a defined ionic strength and pH. Appropriate high stringent hybridization conditions include, e.g., hybridization in a buffer such as, for example, 6×SSPE-T (0.9 M NaCl, 60 mM $NaH_2PO_4$, 6 mM EDTA and 0.05% Triton X-100) for between about 10 minutes and about at least 3 hours (in one embodiment, at least about 15 minutes) at a temperature ranging from about 4° C. to about 37° C.). In one embodiment, hybridization under high stringent conditions is carried out in 5×SSC, 50% deionized Formamide, 0.1% SDS at 42° C. overnight.

Hybridization can be performed on preparations that are affixed to a solid support or in solution, to in situ tissue preparations, etc. One type of hybridization analysis is annealing to oligonucleotide probes which are immobilized on a suitable surface, such as a functionalized glass slide, a nylon support, or a chip, e.g. in an array. Hybridization conditions are chosen that are appropriate for the length and composition of the probe and the method of hybridization.

Other conventional methods to detect (e.g., quantify) amplified nucleic acids will be evident to a skilled worker. These include, e.g., ELISA detection using biotinylated or modified primers, dot blotting, differential hybridization, subtractive hybridization, or the like.

In another embodiment of the invention, the amounts of the mRNAs are determined indirectly by measuring the amount of polypeptide translated from the mRNAs. Generally, in such methods, antibodies are used which are specific for a region of interest in the polypeptide.

As noted above, alternative intron/exon a, located from nucleotides 2131-2166 can be spliced out of hTERT mRNA. A polypeptide translated from such an RNA is deleted for 12 amino acids (which are represented by SEQ ID NO:6); this deletion removes reverse transcriptase motif A. The presence or absence of this spliced mRNA can be determined, e.g., by reacting polypeptide in a sample from a subject with an antibody that is specific for an epitope within this 12 amino acid sequence, under conditions in which the antibody reacts specifically with polypeptides that comprise this epitope. Another of the variant sequences, the β-deletion at nts 2286-2468, encodes a truncated protein, due to a reading frame-shift at base 2287, which is joined to nt 2469, and subsequently a termination codon at nt 2605. This variant protein has reverse transcriptase domains 1, 2, A, B', and part of C. In order to detect the presence or absence of this deletion, one can react polypeptides in a sample from a subject with an antibody that is specific for an epitope within the 61 amino acid polypeptide translated from the deleted sequence (this 61 amino acid sequence is represented by SEQ ID NO:4). Alternatively, one can use an antibody specific for amino acids that lie downstream of the termination codon; mRNAs having the β-deletion will not generate a polypeptide having this sequence, whereas mRNAs having the β-sequence will encode and translate those amino acid sequences. In any of these assays, it is preferable to react polypeptides in the sample from the subject with a positive control antibody, which will hybridize to a portion of the TERT protein that is expected to be present in proteins translated from both RNAs which lack and which comprise the deleted sequence. For example, antibodies can be used which are specific for epitopes of polypeptides translated from exon 4 (RT domains 1 and 2). Other suitable positive control antibodies will be evident to a skilled worker.

Antibodies suitable for use in assays of the invention are commercially available, or can be prepared routinely. Methods for preparing and using antibodies in assays for polypeptides of interest are conventional, and are described, e.g., in Green et al., Production of Polyclonal Antisera, in *Immunochemical Protocols* (Manson, ed.), (Humana Press 1992); Coligan et al., in *Current Protocols in Immunology, Sec.* 2.4.1 (1992); Kohler & Milstein (1975), *Nature* 256, 495; Coligan et al., sections 2.5.1-2.6.7; and Harlow et al., Antibodies: A Laboratory Manual, page 726 (Cold Spring Harbor Laboratory Pub. 1988).

Any of a variety of antibodies can be used in methods of the invention. Suitable antibodies include, e.g., polyclonal, monoclonal (mAbs), recombinant, humanized or partially humanized, single chain, Fab, and fragments thereof. The antibodies can be of any isotype, e.g., IgM, various IgG isotypes such as $IgG_1$, $IgG_{2a}$, etc., and they can be from any animal species that produces antibodies, including goat, rabbit, mouse, chicken or the like. The term, an antibody "specific for" a polypeptide, means that the antibody recognizes a defined sequence of amino acids, or epitope, in the polypeptide, and binds selectively to the polypeptide and not generally to polypeptides unintended for binding to the antibody. The parameters required to achieve specific binding can be determined routinely, using conventional methods in the art. Antibodies are generally accepted as specific against telomerase protein if they bind with a $K_d$ of greater than or equal to $10^{-7}$ M, preferably greater than of equal to $10^{-8}$ M. The affinity of a monoclonal antibody or binding partner can be readily determined by one of ordinary skill in the art (see, e.g., Scatchard (1949) *Ann. N.Y. Acad. Sci.* 51, 660-6672).

In one embodiment of the invention, antibodies specific for a (one or more) polypeptide of the invention are immobilized on a surface (e.g., are reactive elements on an array, such as a microarray, or are on another surface, such as used for surface plasmon resonance (SPR)-based technology, such as Biacore), and polypeptide or regions of interest in a polypeptide in the sample are detected by virtue of their ability to bind specifically to the antibodies. Alternatively, polypeptides in the sample can be immobilized on a surface, and detected by virtue of their ability to bind specifically to the antibodies. Methods of preparing the surfaces and performing the analyses, including conditions effective for specific binding, are conventional and well known in the art. In one embodiment of the invention, the antibody is contacted with a histological preparation (e.g. from a thyroid tumor or lymph node biopsy), and the amount of polypeptide is determined by immunohistochemical staining (e.g., in situ).

Among the many types of suitable immunoassays are immunohistochemical staining, immunocytochemical staining, ELISA, ELISPOT, Western blot (immunoblot), immunoprecipitation, radioimmuno assay (RIA), immunofluorescence (e.g., fluorescence-activated cell sorting (FACS)), immunoprecipitation, etc. Assays used in a method of the invention can be based on colorimetric readouts, fluorescent readouts, mass spectroscopy, visual inspection, etc. Assays can be carried out, e.g., with suspension beads, or with arrays, in which antibodies or cell or blood samples are attached to a surface such as a glass slide or a chip.

A method of the invention can be combined with additional tests to determine if a thyroid tumor is malignant. For example, a sample can be further tested to determine if it contains a mutation in the BRAF gene (a serine-threonine kinase), wherein the presence of the mutation is further indicative that the tumor is malignant. (See, e.g., Cheng et al. (1998) *Br J Cancer* 77, 2177-2180.) Alternatively, a method of the invention can be combined with an assay for any of the splice variants shown in Tables 3 and 4, wherein a significantly increased amount of one or more of the splice variants in Table 3, or a significantly decreased amount of one or more of the splice variants in Table 4 further indicates that the thyroid tumor is malignant. Moreover, a sample can be further tested to determine if it contains a significantly increased or decreased amount of expression of one of the genes that the present inventors have shown to be correlated with malignancy of thyroid tumors. In a paper recently published by some of the present inventors and their colleagues (Prasad et al. (2008) *Clin Cancer Res* 14, 3327-37), nine genes were identified which are statistically overexpressed in malignant thyroid tumors (HMGA2, PLAG1, CDH3, SPOCK1, CEACAM6, DPP4, PRSS3, PDESA and LRRK2), and three genes were identified which are statistically under-expressed in malignant thyroid tumors (RAG2, AGTR1 and TP05). The degree of expression of these genes can also be used to further determine whether a thyroid tumor being tested is malignant or benign.

In one embodiment of the invention, if a subject is determined by a method of the invention to be likely to have a malignant thyroid tumor, a decision can be made to treat the subject with an aggressive form of treatment; and, in one embodiment, the aggressive treatment is then administered. Suitable aggressive treatment modalities include, for example, a total or near-total thyroidectomy and optionally, following the surgery, treatment with radioactive iodine or treatment with a targeted agent. By contrast, if a subject is determined not to be likely to have a metastatic tumor, a decision can be made not to treat the subject further, or to adopt a less aggressive treatment regimen. In one embodiment, the subject is then treated with less aggressive forms of treatment. Suitable less aggressive forms of treatment, which are appropriate for benign lesions, include, for example, a thyroid lobectomy. A subject that does not have a metastatic thyroid tumor is thus spared the unpleasant side effects associated with the unnecessary, more aggressive forms of treatment. By "treated" is meant that an effective amount of an agent such as radioiodine or other anti-cancer procedure is administered to the subject. An "effective" treatment refers to a treatment that elicits a detectable response (e.g. a therapeutic response) in the subject.

A detection (diagnostic) method of the invention can be adapted for many uses. For example, it can be used to monitor the response to a treatment. For example, after a total thyroidectomy has been performed and the subject has been treated with radioactive iodine or another treatment, a sample from the subject (e.g., blood or a lymph node sample) can be assayed to determine the relative amount of TERT mRNA which comprises or lacks the β sequence. A subject can be monitored in this way to determine the effectiveness for that subject of a particular drug regimen; or a drug or other treatment modality can be evaluated in a pre-clinical or clinical trial. In these methods, a relative increase in the amount of TERT mRNA lacking the β sequence compared to the amount of TERT mRNA comprising the sequence is indicative of effective treatment.

A method of the invention can be adapted to identify an agent for treating a thyroid tumor. In one embodiment, a population of thyroid cells (e.g., cells in culture or in a tumor in an animal model, such as a conventional mouse model for thyroid cancer) that has been determined by a method of the invention to be malignant is contacted with a test agent; and the mRNA expression pattern is determined after a designated period of time of treatment with the agent. An agent that can alter the expression pattern to be more like the expression pattern of a non-malignant thyroid tumor is a candidate for an agent to treat malignant thyroid cancer.

One aspect of the invention is a kit for detecting whether a thyroid tumor is likely to be malignant, comprising one or more agents for detecting the amount of a spliced mRNA of the invention (e.g., the by measuring the amount of the mRNA, and/or the amount of a polypeptide encoded by it). As used herein, the singular forms "a," "an" and "the" include plural referents unless the context clearly dictates otherwise. For example, "an" mRNA of the invention, as used above, includes 1, 2, 3, 4, 5 or more of the mRNAs. The agents in the kit can encompass, e.g., probes specific for the mRNA that can be used to hybridize to the RNA (or to a cDNA or PCR product generated from it) or specific primers for performing RT-PCR, or antibodies specific sequences of interest in the polypeptides. The kit may also include additional agents suitable for detecting, measuring and/or quantitating the amount of nucleic acid or polypeptide. Among other uses, kits of the invention can be used in experimental applications. A skilled worker will recognize components of kits suitable for carrying out a method of the invention.

Optionally, a kit of the invention may comprise instructions for performing the method. Optional elements of a kit of the invention include suitable buffers, containers, or packaging materials. The reagents of the kit may be in containers in which the reagents are stable, e.g., in lyophilized form or stabilized liquids. The reagents may also be in single use form, e.g., for the performance of an assay for a single subject.

In the foregoing and in the following examples, all temperatures are set forth in uncorrected degrees Celsius; and, unless otherwise indicated, all parts and percentages are by weight.

EXAMPLES

Example I. Materials and Methods

A. Tumor Tissues

One hundred and thirty three thyroid tumors were collected under Johns Hopkins Institutional Review Board approval from patients undergoing thyroid surgery. Samples included 60 malignant (28 papillary thyroid cancers, 24 follicular variant of papillary thyroid cancers, 5 follicular cancers, and 3 Hürthle cell cancers) and 73 benign lesions (31 adenomatoid nodules, 21 follicular adenomas, 12 Hürthle cell adenomas, and 9 Hashimoto's thyroiditis nodules). Follicular and Hürthle cell cancers are relatively infrequent thyroid tumors resulting in the limited sample numbers. Samples were snap frozen in liquid nitrogen and stored at −80° C. until use. Among these 133 samples, a subset of 50 tumors had suspicious FNA cytology reports.

B. RT- and Nested PCR

Figure 1B:
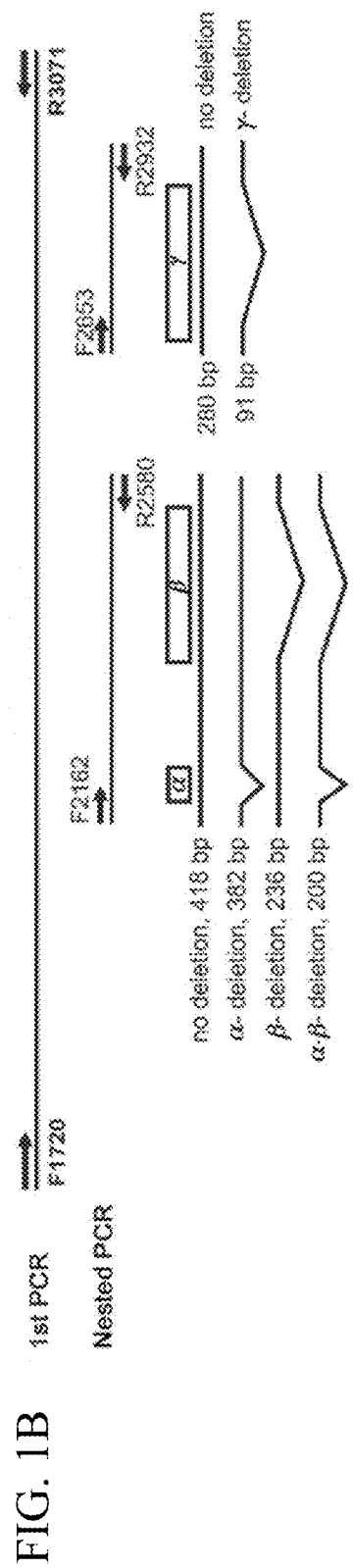

Total RNA was isolated from each tumor with Trizol (Invitrogen, Carlsbad, Calif.) and purified with RNeasy Mini Kit (Qiagen, Valencia, Calif.). Reverse transcription was performed with 1 µg of total RNA and oligo(dT) primers by SuperScript II reverse transcriptase (Invitrogen). hTERT alternative splice variants were amplified by nested PCR using primers designed according to GenBank accession No. AF015950 (FIG. 1B). The first round of amplification spanned a region that included all α-, β-, and γ-deletion sites with forward primer F1720, 5'-GCTGCTCAG-GTCTTTCTTTTAT-3' (SEQ ID NO:7) and reverse primer R3071, 5'-GGAGGATCTTGTAGATGTTGGT-3' (SEQ ID NO:8). PCR was performed in 25 µl of reaction mixture using 1 µl of the cDNA, Platinum Taq DNA polymerase (Invitrogen) by incubation at 94° C. for 2 minutes, followed by 25 amplification cycles of 94° C. for 30 seconds, 54° C. for 30 seconds, and 72° C. for 90 seconds, and a final extension at 72° C. for 5 minutes. The second round of PCR was carried out with 1 µl of the first round PCR product, nested primer sets, and the Platinum Taq DNA polymerase. The nested primer set for hTERT α- and β-transcript variants, variants, forward F2162 5'-CCGCCTGAGCTG-TACTTTGTC-3' (SEQ ID NO:9) and reverse R2580 5'-CA-GAGCAGCGTGGAGAGGAT-3' (SEQ ID NO:10), produced four possible products: $\alpha^+\beta^+$ (418-bp), $\alpha^-\beta^+$ (382-bp), $\alpha^+\beta^-$ (236-bp), and $\alpha^-\beta^-$ (200-bp) respectively by incubation at 94° C. for 2 minutes, followed by 25 amplification cycles of 94° C. for 20 seconds, 57.3° C. for 20 seconds, and 72° C. for 30 seconds, and a final extension at 72° C. for 2 minutes. The hTERT γ-transcript was amplified using the nested primer set, forward F2653 5'-GGTGGAT-GATTTCTTGTTGGT-3' (SEQ ID NO:11) and reverse R2932 5'-GGTGAGACTGGCTCTGATGG-3' (SEQ ID NO:12), yielding 2 possible products: 280-($\gamma^+$) and 91-bp ($\gamma^-$) in length, by incubation in a similar fashion with the exception of a different annealing temperature of 55.5° C. Amplified products were electrophoresed on 2% agarose gels with Nucleic Acid Gel Stain (Cambrex, Rockland, Me.) and visualized under ultraviolet light. The densitomehic value of each hTERT transcript was quantified using Quantity One image analysis software (version 4.5.2; BioRad, Hercules, Calif.). The relative gene expression level of each transcript was reported as a relative proportion of all the hTERT transcripts present in the same sample (28). GAPDH served as an internal control.

C. Statistical Analysis

For analysis of the hTERT alternative splice variant data in thyroid tumors, the following comparisons were performed: 1) between malignant (n=60) and benign (n=73) thyroid tumors and, 2) between malignant (n=19) and benign (n=31) thyroid lesions that had corresponding suspicious or indeterminate FNA cytology. These cytologies included: suspicious for papillary thyroid cancer or follicular variant of papillary thyroid cancer, thyroid neoplasm, follicular neoplasm, Hürthle cell neoplasm, and neoplasm. Because the data were recorded as the proportion of transcripts in each respective gel lane (full-length, α-, and β-/α-β-deletion), a comparison of equal proportions between tumor types was done. This comparison was based on a standardized difference statistic in multinomial probabilities and tested using a permutation approach. For the purpose of analysis, the α-β-deletion was considered in the same category as the β-deletion since both variants produce non-functional proteins.

D. Receiver Operating Characteristic (ROC) Analysis

An ROC analysis was done to evaluate the use of relative proportions of hTERT splice variants to classify tumors as either benign or malignant. The following three splice variants were quantified: 1) full-length hTERT transcript; 2) α-deletion transcript and 3) β-/α-β-deletion transcript (β-/α-β-deletion was defined as the sum of relative proportions for β- and α-β-deletion transcripts). Since the three ROC curves corresponding to each transcript (full, α- and β-/α-

β-deletions) were from the same sample, the method of Delong et al [(1988) *Biometrics* 44, 837-845] was implemented for the comparison of estimated areas under each curve. Once a transcript variant was identified as a preferable diagnostic tool, thresholds were reported for 1) simultaneously maximizing sensitivity and specificity (Gallop et al. (2003) *Understanding Statistics* 2, 219-242) and, 2) maximizing specificity while also retaining a sensitivity greater than 50%. This second approach was chosen to minimize the probability of false positives, since FNA already provides a high level of sensitivity.

E. Quantitative Telomerase Enzyme Activity Assay

Telomerase enzyme activity assay was performed on a subset of 16 of the 133 samples using the Quantitative Telomerase Detection Kit (US Biomax, Inc, Ijamsville, Md.) and according to the manufacturer's instructions. Briefly, for each sample, protein from twelve 10 μm cryosections was extracted in 100 μl CHAPS lysis buffer at 4° C. The protein concentration was determined using Bio-Rad Protein Assay (Bio-Rad Laboratories). Heat-inactivated controls were performed by pre-incubating extracts at 85° C. for 10 minutes. For each assay 1 μg protein was added to a 25 μl QTD reaction mix. Reactions were performed in 96-well plates on an ABI prism 770-sequence detector. The extension reactions were run for 20 minutes at 25° C., followed by 40 cycles of PCR amplification and a melting curve analysis performed. A standard curve was constructed using a dilution series of the telomerase standard substrate provided by the manufacturer and used to calculate relative amounts of the TRAP assay product. The reaction products were then electrophoresed on a 10% polyacrylamide gel and the telomerase hexamer ladders visualized by ethidium bromide staining.

F. Real-Time PCR for c-Myc

Real-time RT-PCR for c-myc was performed on a subset of 23 of the 133 samples using the synthesized first-strand cDNA from total RNA isolated from thyroid tumors. Assays-on-demand Gene Expression products were used for c-myc (Hs00153408_m1) and GAPDH (Hs99999905_m1) (Applied Biosystems, Foster City, Calif.). Reactions were performed in a 20 μl reaction volume containing 1×Taq Man universal PCR master mix (Applied Biosystems), 1× Gene expression assay mix (primers and TaqMan MGB probe dye-labeled with FAM) and 1 μl cDNA. Reactions were performed on an ABI7300HT sequence detection system machine (Applied Biosystems). All PCR reactions were performed in triplicate. Fluorescence was quantified with the Sequence detection system software, version 2.0 (Applied Biosystems).

Example II. Results of Studies of hTERT Alternative Splice Patterns

A. hTERT Alternative Splice Variant Patterns in Thyroid Tumors hTERT gene expression was detected in 114 of the 133 (86%) thyroid tumors (Table 1).

TABLE 1

Thyroid Tumors Analyzed for hTERT alternative splice variant patterns by subtype

| Final Histology | Malignant (n = 60) | | | | Benign (n = 73) | | | |
| --- | --- | --- | --- | --- | --- | --- | --- | --- |
| | PTC (n = 28) | FVPTC (n = 24) | FC (n = 5) | HC (n = 3) | FA (n = 21) | AN (n = 31) | HA (n = 12) | LcT (n = 9) |
| hTERT positive (n = 114) | 28 | 21 | 3 | 1 | 21 | 25 | 6 | 9 |
| hTERT full-length >0.33$^a$ (n = 41) | 24 (86%) | 4 (19%) | 3 (100%) | 1 (100%) | 1 (5%) | 1 (4%) | 4 (67%) | 3 (33%) |

Figure 2A:
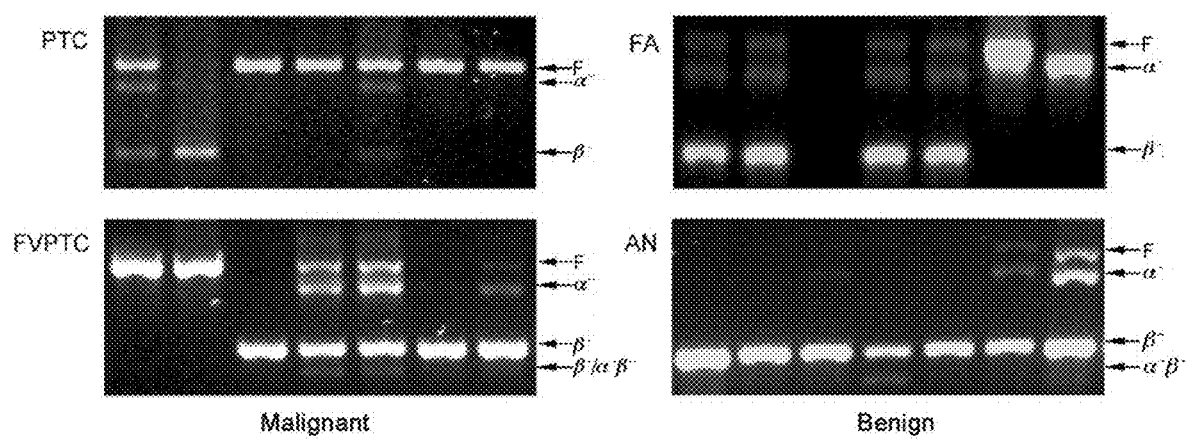
FIG. 2A-2B shows hTERT alternative splice variant patterns in thyroid tumors.

$^a$An hTERT full-length expression cut point of 0.33 corresponded to a specificity of 0.85 and a sensitivity of 0.60.
AN, adenomatoid nodule;
FA, follicular adenoma;
FC, follicular carcinoma;
FVPTC, follicular variant of papillary thyroid carcinoma;
HA, Hurthle cell adenoma;
HC, Hurthle cell carcinoma;
LcT, lymphocytic thyroiditis nodule;
PTC, papillary thyroid carcinoma No tumor exhibited γ-deletion splice variant and only 4/133 exhibited an α-β-deletion variant. Representative gels are shown in FIG. 2A. The hTERT splice variant patterns present in papillary thyroid cancers, follicular variant of papillary thyroid cancers, follicular adenomas, and adenomatoid nodules (the 4 most common tumor types that can be suspicious on thyroid FNA) are depicted. The gels demonstrate the prominent presence of full-length hTERT gene expression in papillary thyroid cancer and the progressive loss thereof in follicular variant of papillary thyroid cancer and the benign tumors (follicular adenoma and adenomatoid nodule). Note that "full-length" hTERT gene expression, as used in this Example, refers to mRNA corresponding to the PCR product generated by the nested primers, wherein the mRNA does not exhibit the α-, β-, or α plus β-deletions. There is also a concomitant gain of the inhibitory α-deletion, non-functional β- and α-β-deletion patterns in the benign tumors.

B. Statistical Analysis of all Thyroid Nodules

Overall, we found significant differences in the proportions of the various transcripts between malignant and benign thyroid tumors (p<0.001). On average, the malignant tumors exhibited larger proportions of full-length hTERT transcripts (0.57±0.15) than either the α-(0.13±0.02), or β-/α-β-deletion transcripts (0.30±0.11, FIG. 2B). This was true for all malignant tumor types except follicular variant of papillary thyroid cancer. In contrast, the benign tumors exhibited greater proportions of β-/αβ-deletion transcripts (0.64±0.08) than either the full-length (0.19±0.06) or α-deletion transcripts (0.17±0.02, FIG. 2B).

C. Analysis of Suspicious Thyroid Nodules

In a subset analysis, we repeated our hTERT splice variant assay on 50 thyroid tumors with the preoperative diagnosis of suspicious FNA (Table 2), the cytological category most in need of additional molecular diagnostic tools. Thirty-eight of the 50 (76%) were hTERT positive. The results in this subset were similar to the original cohort, with malignant tumors exhibiting greater proportions of full-length transcripts compared to α- and β-/α-β-deletion transcripts, while among the benign tumors (with the exception of Hürthle cell adenomas), greater proportions of β-/α-β-deletion transcripts were observed compared to full-length or α-deletion transcripts.

the benign samples. Furthermore, only alternative splice variant patterns showing a preponderance of full-length transcript were significantly associated with high levels of telomerase enzyme activity test: $\chi^2=0.02$, FIG. 3B).

F. c-Myc Expression and hTERT Alternative Splice Variant Patterns

Figure 4:
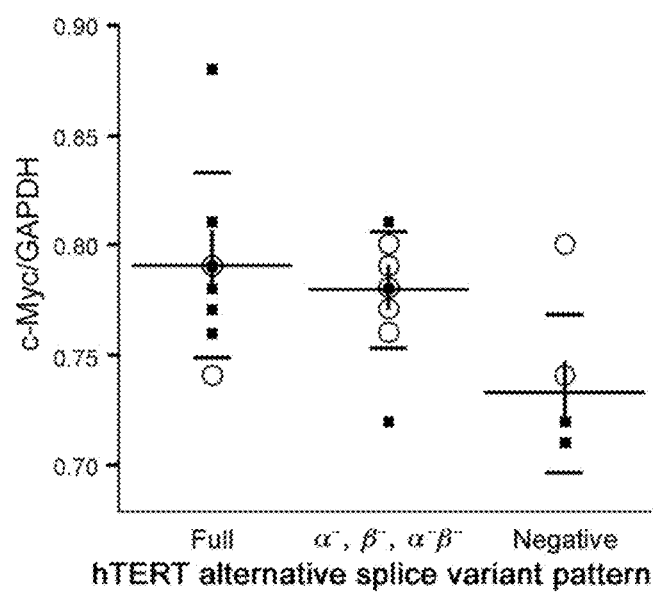
FIG. 4 shows c-Myc gene expression vs. hTERT alternative splice variant patterns. The ratios of c-myc and GAPDH mRNA levels determined by real time RT-PCR are shown for the three categories of hTERT splice variants. Long horizontal bars represent means; vertical bars, the standard error of the means; and short bars, standard deviations. (v), malignant tumors; (O), benign tumors.

Next, we studied the correlations between c-myc and hTERT gene expression. Similar to others, we observed a statistically significant association between c-myc and hTERT gene expression positive samples. However, we also documented that this correlation did not vary among the different specific splice variant patterns (FIG. 4). Of the 23 samples tested for c-myc gene expression (13 malignant and

TABLE 2 hTERT Gene Expression in the Subset of Thyroid Nodules with Preoperative Suspicious FNA Diagnosis

| | Malignant (n = 19) | | | | Benign (n = 31) | | | |
|---|---|---|---|---|---|---|---|---|
| Final Histology | PTC (n = 4) | FVPTC (n = 9) | FC (n = 5) | HC (n = 1) | FA (n = 14) | AN (n = 4) | HA (n = 8) | LcT (n = 1) |
| hTERT positive (n = 38) | 4 | 9 | 3 | 1 | 14 | 4 | 2 | 1 |
| hTERT full-length >0.59[a] (n = 11) | 4 | 1 | 3 | 1 | 1 | 0 | 1 | 0 |

[a]An hTERT full-length expression cut point of 0.59 corresponded to a specificity of 0.90 and a sensitivity of 0.53.
AN, adenomatoid nodule;
FA, follicular adenoma;
FC, follicular carcinoma;
FNA, fine needle aspiration;
FVPTC, follicular variant of papillary thyroid carcinoma;
HA, Hurthle cell adenoma;
HC, Hurthle cell carcinoma;
LcT, lymphocytic thyroiditis nodule;
PTC, papillary thyroid carcinoma D. Receiver Operating Characteristic (ROC) Analysis Altogether, 114 cases that were hTERT gene expression-positive were included in the ROC analysis. Since malignant tumors exhibited a greater proportion of full-length transcripts, we focused on this transcript as a diagnostic tool, and this approach resulted in an area under the curve (AUC) of 0.79. Based on the simultaneous maximization method, a full-length transcript threshold of 0.22 corresponded to a sensitivity and specificity of 0.74. Similar results were observed for the 38 hTERT positive samples from the subset with suspicious FNAs, with an estimated AUC of 0.69 and, based on a full-length threshold of 0.17, a sensitivity and specificity of 0.67.

In addition to the above approach using equal maximization of sensitivity and specificity, we also examined the full-length threshold associated with the largest observed specificity for a given sensitivity no less than 0.50. By applying these criteria to all samples, a full-length transcript threshold of 0.33 achieved a specificity of 0.85 for a given sensitivity of 0.60 (Table 1). Among the subset of suspicious thyroid nodules, a full-length threshold of 0.59 corresponded to a specificity of 0.90 for a given sensitivity of 0.53 (Table 2), thereby providing a diagnostic strategy with a very high specificity.

E. Quantitative Telomerase Enzyme Activity Analysis

We also tested a subset of 16 thyroid tumors for functional telomerase activity. The malignant tumors (n=8) showed significantly higher average telomerase enzyme activity (FIG. 3A) than the benign samples (n=8) (t test: p=0.03). Several of the thyroid cancers that exhibited minimal capsular invasion or follicular variant of papillary thyroid cancer morphology had telomerase activity values similar to 10 benign), the following three groups were defined: 1) full-length hTERT (n=8); 2) α- and β-/α-β-deletion variants hTERT (n=9); and 3) negative hTERT (n=6). A comparison of mean differences between each pair of groups, with respect to c-myc gene expression, was conducted based on a chi-squared test. No difference was seen between full-length and α- and β-/α-β-deletion variants. However, a significant difference in mean c-myc was observed between negative and full-length hTERT groups (p=0.003) and between negative and α- and β-/α-β-deletion variant groups (p=0.018). These data suggest that c-myc gene expression correlates with overall hTERT gene expression, regardless of whether or not hTERT is expressed in its active form.

Discussion

We examined the patterns of hTERT alternative splice variants in an effort to discern differences between benign and malignant thyroid tumors. Because hTERT expression was low in most of the samples, the target concentration produced from a single conventional PCR within 30 cycles was often too low to be detected. Nonspecific products are frequently generated by increasing the amplification cycles with a single set of primers, even with a hot start. Furthermore, quantitative real time PCR is not applicable for the evaluation of 4 different hTERT isoforms. We therefore chose to use nested PCR in order to: 1) increase the sensitivity of the assay to be able to detect each splice variant and 2) as an effective solution to PCR nonspecificity and gene copy limitation. One major concern about nested PCR is that it does not maintain a linear relationship between the amount of final amplified product and the amount of target sequence. Studies indicate, however, that nested PCR will retain its utility for quantitation if the first round PCR is maintained in the exponential phase (Zieger et al. (2005) *J Surg Oncol* 89, 108-113). Indeed, quantitative nested real-time PCR assay has been developed and used in some studies without apparent distortion in the amplified product ratio (Renshaw et al. (2002) *Am J Clin Pathol* 117, 19-21). Furthermore, we also optimized our nested PCR reaction using thyroid cell lines to ensure accurate product ratios. In our study, primers specific for each of the hTERT isoforms were used in the nested PCR. Our results clearly demonstrate significant differences in the patterns of functional and non-functional hTERT transcripts in benign vs. malignant tumors.

Figure 2B:
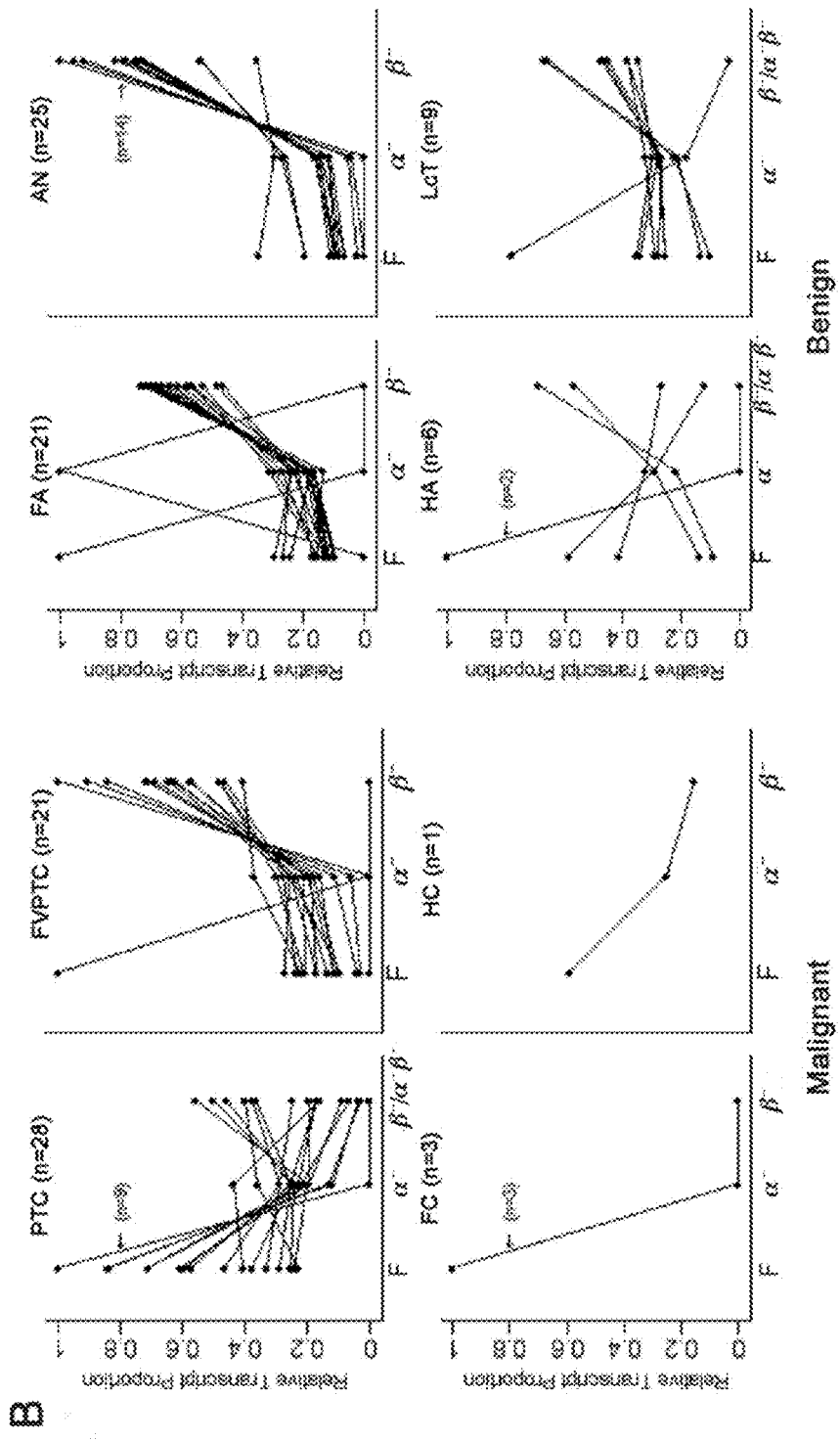

With the exception of follicular variant of papillary thyroid cancer, the malignant tumors exhibited a greater proportion of the hTERT full-length transcript compared to either the α-, or β-/α-β-deletions, whereas the benign tumors exhibited a greater proportion of the β-/α-β-deletion transcripts compared to the full or α-deletion (FIG. 2B). The fact that follicular variant of papillary thyroid cancer showed comparably less full-length transcript than the other thyroid malignancies is in keeping with the notion that the histological evaluation of these tumors is often problematic, with inter-observer variation present up to 60% of the time.

One objective for testing thyroid tumors for differences in hTERT patterns was to improve the specificity of the clinically ambiguous FNA diagnosis of suspicious thyroid lesions. In the 50 tumors that had corresponding suspicious FNA cytology, the same patterns seen in the 133 tumors were observed with the exception of Hürthle cell adenomas. Indeed, ROC analysis revealed that a full-length transcript proportion over 0.33 yielded a specificity of 85% in the diagnosis of thyroid malignancy. Furthermore, setting the cut point of the full-length transcript proportion at 0.59 in the subset with suspicious FNA reports yielded 90% specificity.

Example III. Identification of Other Splice Variants Associated with Malignant or Non-Malignant Thyroid Tumors A. Splice Array Analysis Twenty one thyroid tumors were analyzed by splice array analysis. Three each of papillary thyroid cancer, follicular variant of papillary thyroid cancer, follicular cancer, adenomatoid nodule, follicular adenoma, Hürthle cell adenoma, and lymphocytic thyroiditis nodule, plus corresponding normal thyroid samples were hybridized to Human Genome Wide SpliceArray™ (ExonHit Therapeutics, Inc., Gaithersburg, Md.) on the Affymetrix platform.

In brief, the splice array analysis was carried out as follows:

Transcript Amplification and Labeling:

Amplified, labeled cDNA was prepared using the NuGEN WT-Ovation™ Pico RNA Amplification System and the FL-Ovation™ cDNA Biotin Module V2. First strand cDNA was prepared from total RNA using a unique first strand DNA/RNA chimeric primer mix and reverse transcriptase (RT). The primers have a DNA portion that hybridizes either to the 5' portion of the poly (A) sequence or randomly across the transcript. RT extends the 3' DNA end of each primer generating first strand cDNA. Fragmentation of the mRNA within the cDNA/mRNA complex creates priming sites for DNA polymerase to synthesize a second strand, which includes DNA complementary to the 5' unique sequence from the first strand chimeric primers. The result is a double stranded cDNA with a unique DNA/RNA heteroduplex at one end that is isothermally amplified using the SPIA™ process, developed by NuGEN™. The process includes a SPIA™ DNA/RNA chimeric primer, DNA polymerase and RNase H in a homogeneous isothermal assay that provides highly efficient amplification of DNA sequences. An average mRNA amplification of 15,000-fold is observed with 500 pg of starting total RNA.

Array Hybridization, Scanning, and Data Extraction:

Standard methods following recommendations of the manufacturer were used to hybridize the samples to the Splice Arrays. The arrays were stained and washed using the FS450-001 fluidics protocol prior to scanning with the Affymetrix GeneChip® Scanner 3000 7G. DAT and .CEL images were then visually inspected for anomalies and accurate grid placement.

Figure 5A:
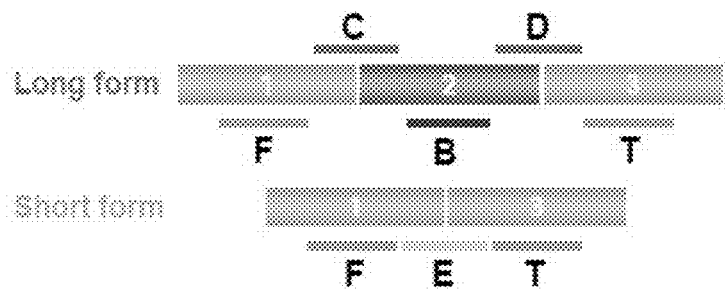
FIG. 5A shows the splice array probe configuration for each known and predicted splicing event.
Figure 5B:
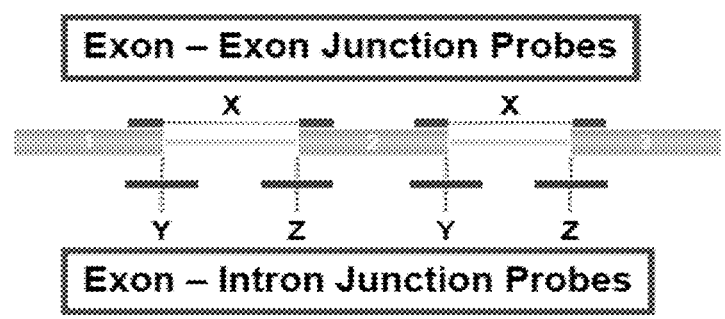
FIG. 5B shows the configuration for intron retention splicing event (as prepared by Exonhit Therapeutics, Inc.).

Three samples from the malignant thyroid subtype, Hürthle cell cancer, did not pass quality control specifications and thus, were not tested. Briefly, total RNAs were isolated from tumor and normal thyroid and, reverse transcribed with random primers prior to PCR amplification. The PCR products were then enzymatically fragmented and labeled at their 3' termini. The resulting products were hybridized to SpliceArrays containing over 6,000,000 probes representing 138,000 known or predicted splice events (FIGS. 5A and 5B). The different splice events tested for include the following: alternative exons in which exons are either: 1) skipped or 2) included; 3) alternative 5' (donor) and 4) 3' (acceptor) splice sites; and; 5) retained introns.

B. Overall Analytical Approach:

Given the complexity of analyses of our exon expression data, the possibility of 5 different events for each exon, and 7 different thyroid subtypes we chose the following overall approach. We first selected probes with statistically significant differential expression between each tumor type and corresponding matched normal thyroid; these results were then used to filter expression heterogeneity among subtypes within the same class (malignant or benign) by applying a novel query-based comparisons algorithm (Kowalski et al. *From Ambiguities to Insights in Cancer Diagnosis via Query-based Comparisons*. Pattern Recognition, 2008. doi: 10.1016/j.patcog.2008.09.030). The objective of this second screen was to select genes that characterized specific tumor subtype pairs within each class to ultimately select genes that characterize the benign and malignant classes overall.

C. Normalization of Array Data:

The array data were normalized by Partek's Genomics Suite software while importing the 42 .CEL files. Data were first processed using GC content background correction followed by Robust Multichip Average (RMA) background correction (Marme et al. (2008) *Int J Cancer* 123, 2048-56). Quantile normalization was performed across all 42 arrays (21 tumors and 21 matched normal thyroid). Data were Log 2 transformed and mean probe summarization was applied. The data set was filtered based on the expression values' frequency distribution in order to remove probe sets that were expressed at a low level. A probe was removed if all of the samples' intensity values fell below the pre-determined Log 2 based value of (4.3).

D. Within Class and within Subtype, Probe Analyses.

Two-way Analysis of Variance (ANOVA) models were used to perform statistical tests on the filtered expression values, comparing each tumor type against its respective matched normal tissue. The overall signal intensity values showed a normal distribution following Partek default processing for all samples analyzed. This comparison resulted in lists of differentially expressed transcripts, based on a fold change of 1.8 (p-value ≤0.001). Within malignant tumor subtypes, 822 distinct Entrez gene IDs were selected as showing significantly different splice variant expression in papillary thyroid cancers vs. matched normal, 889 in follicular variant of papillary thyroid cancer, and 885 in follicular cancer. For the benign tumor subtypes, 884 distinct gene IDs were selected as significantly different in adenomatoid nodule tumors vs. matched normal; 550 in follicular adenoma, 824 in Hürthle cell adenoma and 606 in lymphocytic thyroiditis nodule.

E. Within Class and Between-Subtypes, Heterogeneity Analyses.

Using papillary thyroid cancer as the 'common' malignant thyroid tumor subtype, we paired it with each other subtype (follicular variant of papillary thyroid cancer and follicular cancer), in order to identify significantly expressed splice variants that were common between each pair. We then compared results across all pairs to identify splice variants in common to all 3 malignant tumors. We identified 69 distinct Entrez genes that were common to papillary thyroid cancer and follicular cancer; 81 common to papillary thyroid cancer and follicular variant of papillary thyroid cancer; and 25 common to all 3 subtypes (Table 3). Similarly, by using adenomatoid nodule as the 'common' benign tumor subtype, we paired each other subtype (follicular adenoma, Hürthle cell adenoma, and lymphocytic thyroiditis nodule) and found 38 genes common to adenomatoid nodule and follicular adenoma; 63 common to adenomatoid nodule and Hürthle cell adenoma; 44 common to adenomatoid nodule and lymphocytic thyroid nodule and 2 common to all benign subtypes (Table 4). The 25 genes that characterized malignant tumor subtypes were distinct from the two selected as characterizing benign tumor subtypes. Within the malignant samples, we performed PCA analyses among all splice variants chosen after ANOVA analysis and, for comparison, among the 25 genes selected as characterizing the malignant class. The 25 genes selected accounted for 44% of variability in splice variant expression among malignant samples, whereas all the spice variants identified after the ANOVA analysis accounted for 30% of variability.

F. Biological Function:

Gene Ontology (GO) <http://geneontology.org> analysis of the 25 genes associated with the malignant tumors and the 2 associated with the benign tumors was performed using the Spotfire platform (Tables 3 and 4). This GO analysis software provides a p-value for whether or not the selected genes are randomly represented for each of the many GO functional categories compared to the 20,100 well-characterized genes on the arrays. The 25 malignancy genes represented the following functions (p<0.005): positive regulation of kinase activity (n=3 genes) and receptor activity (n=8); and cellular location categories (p=0.00184): membrane (n=18), plasma membrane (n=7) and external side of plasma membrane (n=3). The 2 benign genes represented the following functions (p<0.005): extracellular matrix organization and biogenesis (n=1), collagen fibril organization (n=1); extracellular matrix structural constituent conferring tensile strength (n=1, p=0.000125); and cellular location categories anchoring collagen (n=1).

G. Summary:

In summary, based on 25 probes, we were able to capture 44% of variability in expression among samples from the 3 malignant subtypes in comparison to 30% based on all probes. Of the 8 genes known to be associated with different types of cancer (ADH1C, AOX1, ETK, KIT, NRCAM, SYNE1. AKR1CL2, and RAINB1), 3 genes (KIT, NRCAM, and SYNE1) have been reported to be significantly associated with thyroid cancer; SYNE1 associated with epigenetic regulation; KIT, a proto-oncogene that encodes a transmembrane receptor tyrosine kinase; and NRCAM, a neuronal system cell-adhesion molecule.

TABLE 3

Exon events selected as commonly, differentially expressed among malignant thyroid tumor subtypes, PTC, FVPTC and FC vs. matched normal tissue.

| Entrez Gene ID | Gene Symbol | Chromosomal Location | Event type |
| --- | --- | --- | --- |
| 126 | ADH1C | Chr 4q23 | exon skipped |
| 316 | AOX1 | Chr 2q33.1 | alternative splice acceptor, exon skipped |
| 727 | C5 | Chr 9q33.2 | exon skipped, intron 27 |
| 953 | ENTPD1 | Chr 10q23.33 | exon skipped, novel exons, alternative splice acceptor, intron 4, intron 6 |
| 1804 | DPP6 | Chr 7q36.2 | exon skipped, novel exon |
| 2042 | EPHA3 | Chr 3p11.2-p11.1 | exon skipped |
| 3803 | KIR2DL2 | Chr 19q13.42 | alternative splice acceptor, alternative splice donor |
| 3815 | KIT | Chr 4q12 | exon skipped, novel exon, intron 4 |
| 4897 | NRCAM | Chr 7q31.1 | exons skipped, intron 5 |
| 6262 | RYR2 | Chr 1q43 | exon skipped, intron 24, alternative splice acceptor |
| 8029 | CUBN | Chr 10p13 | intron 55, alternative splice donor, intron 13, intron 41, exon skipped |
| 9162 | DGKI | Chr 7q33 | intron 9, exon skipped, novel exon |
| 9213 | XPR1 | Chr 1q25.3 | exon skipped, intron 1, intron 14 |
| 9844 | ELMO1 | Chr 7p14.2 | exon skipped |
| 9914 | ATP2C2 | Chr 16q24.1 | exon skipped |
| 10349 | ABCA10 | Chr 17q24.3 | exon skipped |
| 23345 | SYNE1 | Chr 6q25.1-q25.2 | intron retention, exon skipped, intron 62, intron 69 |
| 23348 | DOCK9 | Chr 13q32.3 | intron 46, exon skipped, novel exon, alternative splice acceptor |
| 55755 | CDK5RAP2 | Chr 9q33.2 | intron 23, exon skipped, novel exon, intron 36 |
| 56899 | ANKS1B | Chr 12q23.1 | intron 12, exon skipped |
| 83592 | AKR1CL2 | Chr 10p15.1 | exon skipped, intron 1, novel exons |
| 89797 | NAV2 | Chr 11p15.1 | novel exon, intron 24, exon skipped |
| 93035 | PKHD1L1 | Chr 8q23.1-q23.2 | exon skipped, intron 40, intron 41, intron 74, alternative splice donor |
| 200879 | LIPH | Chr 3q27.2 | intron 7, exon skipped |
| 223117 | SEMA3D | Chr 7q21.11 | exon skipped, intron 12 |

TABLE 4

Exon events selected as commonly, differentially expressed among benign thyroid tumor subtypes, AN, FA, HA, and LcT vs. matched normal tissue.

| Entrez Gene ID | Gene Symbol | Chromosomal Location | Event type |
| --- | --- | --- | --- |
| 23223 | RRP12 | Chr 10q24.1 | exon skipped |
| 1303 | COL12A1 | Chr 6q13-q14.1 | exon skipped, intron 23, intron 27, intron 65 |

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications (including provisional patent application 61/005,593, filed Dec. 5, 2007) cited above and in the figures are hereby incorporated in their entirety by reference.

We claim:

1. A method for determining if a thyroid tumor in a human subject is malignant comprising the steps of:
   (a) measuring in a sample obtained from the subject (i) the amount of full length human telomerase reverse transcriptase (hTERT)) mRNA and (ii) the amount of less than full length hTERT mRNA in the sample using quantitative real time polymerase chain reaction (PCR), wherein the quantitative real time PCR utilizes nested primers comprising SEQ ID NO:9 and SEQ ID NO:10, wherein the less than full length hTERT mRNA comprises (a) hTERT mRNA lacking the alpha sequence; (b) hTERT mRNA lacking the beta sequence; and (c) hTERT mRNA lacking both the alpha and beta sequences;
   (b) identifying the tumor as malignant if the amount of full length hTERT mRNA comprises at least 55% of total hTERT mRNA in the sample and identifying the tumor as not malignant if the amount of less than full length hTERT mRNA comprises at least 55% of total hTERT mRNA in the sample.

2. The method of claim 1, wherein the alpha sequence is the 35 base pair sequence represented by SEQ ID NO:5 and the beta sequence is the 182 base pair sequence represented by SEQ ID NO:3.

3. A method for selecting a treatment method for a subject having a thyroid tumor, comprising determining by a method of claim 1 whether the tumor is malignant and, if the tumor is determined to be malignant, deciding to perform a total thyroidectomy on the subject, but if a tumor is determined not to be malignant, deciding not to perform a total thyroidectomy on the subject.

4. The method of claim 1, wherein the method is carried out both before or at approximately the same time as, and after, an administration of a treatment for thyroid cancer.

5. A method for treating a subject having a thyroid tumor, comprising determining by a method of claim 1 whether the tumor is malignant and, if the tumor is malignant, treating the subject aggressively for thyroid cancer, and if the tumor is determined not to be malignant, not treating the subject aggressively for thyroid cancer.

6. The method of claim 1, wherein in the identification step (b) identifying the tumor as malignant if the amount of full length hTERT mRNA comprises at least 59% of total hTERT mRNA in the sample and identifying the tumor as not malignant if the amount of less than full length hTERT mRNA comprises at least 59% of total hTERT mRNA in the sample.

7. A method for treating a human subject having a malignant thyroid tumor comprising the steps of:
   (a) measuring in a sample obtained from the subject (i) the amount of total hTERT mRNA and (ii) the amount of less than full length hTERT mRNA in the sample using quantitative real time polymerase chain reaction (PCR), wherein the quantitative real time PCR utilizes nested primers comprising SEQ ID NO:9 and SEQ ID NO:10, wherein the less than full length hTERT mRNA comprises (a) hTERT mRNA lacking the alpha sequence; (b) hTERT mRNA lacking the beta sequence; and (c) hTERT mRNA lacking both the alpha and beta sequences; and
   (b) performing a total thyroidectomy on the subject if the amount of full length hTERT mRNA comprises at least 55% of total hTERT mRNA in the sample.

8. The method of claim 7, wherein in the performing step (b) performing a total thyroidectomy on the subject if the amount of full length hTERT mRNA comprises at least 59% of total hTERT mRNA in the sample.

9. A method for determining the effectiveness of a treatment of a subject having a thyroid tumor, comprising performing the method of claim 1 both before or at approximately the same time as, and after, the administration of a treatment for thyroid cancer, wherein the treatment is determined to be effective if the tumor is determined to be not malignant after administration of the treatment, and wherein the treatment is determined not to be effective if the tumor is determined to be malignant after administration of the treatment.

* * * * *

SEQUENCE LISTING

<160> NUMBER OF SEQ ID NOS: 12

<210> SEQ ID NO 1
<211> LENGTH: 3964
<212> TYPE: DNA
<213> ORGANISM: Homo sapiens

<400> SEQUENCE: 1

```
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgccccctcc ttccgccagg tgtcctgcct gaaggagctg     240
gtggcccgag tgctgcagag gctgtgcgag cgcggcgcga gaacgtgct ggccttcggc     300
ttcgcgctgc tggacggggc ccgcggggc ccccccgagg ccttcaccac cagcgtgcgc     360
agctacctgc caacacggt gaccgacgca ctgcggggga gcgggcgtg ggggctgctg     420
ttgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcggggggcag tgccagccga agtctgccgt tgcccaagag gcccaggcgt     720
ggcgctgccc ctgagccgga gcggacgccc gttgggcagg ggtcctgggc ccacccgggc     780
aggacgcgtg gaccgagtga ccgtggtttc tgtgtggtgt cacctgccag acccgccgaa     840
gaagccacct ctttggaggg tgcgctctct ggcacgcgcc actcccaccc atccgtgggc     900
cgccagcacc acgcgggccc cccatccaca tcgcggccac cacgtccctg ggacacgcct     960
tgtccccgg tgtacgccga gaccaagcac ttcctctact cctcaggcga caaggagcag    1020
ctgcggccct ccttcctact cagctctctg aggcccagct gactggcgc tcggaggctc    1080
gtggagacca tctttctggg ttccaggccc tggatgccag ggactccccg caggttgccc    1140
cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg tgtctgtgc ccgggagaag ccccagggct ctgtggcggc ccccgaggag    1320
gaggacacag acccccgtcg cctggtgcag ctgctccgcc agcacagcag ccctggcag    1380
gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcggggctg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
ttttatgtca cggagaccac gttctcaaaag aacaggctct ttttctaccg gaagagtgtc    1740
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tcccccaagcc tgacgggctg cggccgattg tgaacatgga ctacgtcgtg    1920
```

```
ggagccagaa cgttccgcag agaaaagagg gccgagcgtc tcacctcgag ggtgaaggca    1980
ctgttcagcg tgctcaacta cgagcgggcg cggcgcccg gcctcctggg cgcctctgtg    2040
ctgggcctgg acgatatcca cagggcctgg cgcaccttcg tgctgcgtgt gcgggcccag   2100
gacccgccgc ctgagctgta ctttgtcaag gtggatgtga cgggcgcgta cgacaccatc   2160
ccccaggaca ggctcacgga ggtcatcgcc agcatcatca aaccccagaa cacgtactgc   2220
gtgcgtcggt atgccgtggt ccagaaggcc gccatgggc acgtccgcaa ggccttcaag   2280
agccacgtct ctaccttgac agacctccag ccgtacatgc gacagttcgt ggctcacctg   2340
caggagacca gccgctgag ggatgccgtc gtcatcgagc agagctcctc cctgaatgag    2400
gccagcagtg gcctcttcga cgtcttccta cgcttcatgt gccaccacgc cgtgcgcatc   2460
agggcaagt cctacgtcca gtgccagggg atcccgcagg gctccatcct ctccacgctg    2520
ctctgcagcc tgtgctacgg cgacatggag aacaagctgt tgcggggat tcggcgggac   2580
gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attccctgg tgcggcctgc tgctggatac ccggacctg    2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgtttct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca ttttttcctgc gcgtcatctc tgacacggcc   3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag gacagcccag   3300
acgcagctga gtcggaagct cccggggacg acgctgactg ccctggaggc cgcagccaac   3360
ccggcactgc cctcagactt caagaccatc ctggactgat ggccacccgc ccacagccag   3420
gccgagagca gacaccagca gccctgtcac gccgggctct acgtcccagg gagggagggg   3480
cggcccacac ccaggcccgc accgctggga gtctgaggcc tgagtgagtg tttgccgag    3540
gcctgcatgt ccggctgaag gctgagtgtc cggctgaggc ctgagcgagt gtccagccaa   3600
gggctgagtg tccagcacac ctgccgtctt cacttcccca caggctggcg ctcggctcca   3660
ccccagggcc agcttttcct caccaggagc ccggcttcca ctccccacat aggaatagtc   3720
catcccccaga ttcgccattg ttcacccctc gccctgccct cctttgcctt ccaccccac    3780
catccaggtg gagaccctga aaggaccct gggagctctg ggaatttgga gtgaccaaag    3840
gtgtgccctg tacacaggcg aggaccctgc acctggatgg gggtccctgt gggtcaaatt   3900
gggggggaggt gctgtgggag taaaatactg aatatatgag ttttttcagtt ttgaaaaaaa   3960
aaaa                                                                3964
```

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser

-continued

```
1               5                   10                  15
His Tyr Arg Glu Val Leu Pro Leu Ala Thr Phe Val Arg Arg Leu Gly
                20                  25                  30
Pro Gln Gly Trp Arg Leu Val Gln Arg Gly Asp Pro Ala Ala Phe Arg
                35                  40                  45
Ala Leu Val Ala Gln Cys Leu Val Cys Val Pro Trp Asp Ala Arg Pro
 50                  55                  60
Pro Pro Ala Ala Pro Ser Phe Arg Gln Val Ser Cys Leu Lys Glu Leu
 65                  70                  75                  80
Val Ala Arg Val Leu Gln Arg Leu Cys Glu Arg Gly Ala Lys Asn Val
                85                  90                  95
Leu Ala Phe Gly Phe Ala Leu Leu Asp Gly Ala Arg Gly Gly Pro Pro
                100                 105                 110
Glu Ala Phe Thr Thr Ser Val Arg Ser Tyr Leu Pro Asn Thr Val Thr
                115                 120                 125
Asp Ala Leu Arg Gly Ser Gly Ala Trp Gly Leu Leu Leu Arg Arg Val
                130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro Pro His Ala Ser Gly
                180                 185                 190
Pro Arg Arg Arg Leu Gly Cys Glu Arg Ala Trp Asn His Ser Val Arg
                195                 200                 205
Glu Ala Gly Val Pro Leu Gly Leu Pro Ala Pro Gly Ala Arg Arg Arg
                210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
                260                 265                 270
Val Ser Pro Ala Arg Pro Ala Glu Glu Ala Thr Ser Leu Glu Gly Ala
                275                 280                 285
Leu Ser Gly Thr Arg His Ser His Pro Ser Val Gly Arg Gln His His
                290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
                340                 345                 350
Ser Leu Thr Gly Ala Arg Arg Leu Val Glu Thr Ile Phe Leu Gly Ser
                355                 360                 365
Arg Pro Trp Met Pro Gly Thr Pro Arg Arg Leu Pro Arg Leu Pro Gln
                370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
```

```
Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
        835                 840                 845
```

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 182
<212> TYPE: DNA
<213> ORGANISM: Homo sapiens

<400> SEQUENCE: 3
gtctctacct tgacagacct ccagccgtac atgcgacagt tcgtggctca cctgcaggag      60
accagcccgc tgagggatgc cgtcgtcatc gagcagagct cctccctgaa tgaggccagc     120
agtggcctct tcgacgtctt cctacgcttc atgtgccacc acgccgtgcg catcaggggc     180
aa                                                                    182

<210> SEQ ID NO 4
<211> LENGTH: 61
<212> TYPE: PRT
<213> ORGANISM: Homo sapiens

-continued

<400> SEQUENCE: 4

Val Ser Thr Leu Thr Asp Leu Gln Pro Tyr Met Arg Gln Phe Val Ala
1               5                   10                  15

His Leu Gln Glu Thr Ser Pro Leu Arg Asp Ala Val Val Ile Glu Gln
            20                  25                  30

Ser Ser Ser Leu Asn Glu Ala Ser Ser Gly Leu Phe Asp Val Phe Leu
        35                  40                  45

Arg Phe Met Cys His His Ala Val Arg Ile Arg Gly Lys
50                  55                  60

<210> SEQ ID NO 5
<211> LENGTH: 36
<212> TYPE: DNA
<213> ORGANISM: Homo sapiens

<400> SEQUENCE: 5
gtggatgtga cgggcgcgta cgacaccatc ccccag                             36

<210> SEQ ID NO 6
<211> LENGTH: 12
<212> TYPE: PRT
<213> ORGANISM: Homo sapiens

<400> SEQUENCE: 6

Val Asp Val Thr Gly Ala Tyr Asp Thr Ile Pro Gln
1               5                   10

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gctgctcagg tctttctttt at                                            22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaggatctt gtagatgttg gt                                            22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgcctgagc tgtactttgt c                                             21

<210> SEQ ID NO 10
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 10
cagagcagcg tggagaggat                                                    20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtggatgat ttcttgttgg t                                                  21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtgagactg gctctgatgg                                                    20
```